US012599546B2

(12) United States Patent
Kawakami et al.

(10) Patent No.: US 12,599,546 B2
(45) Date of Patent: Apr. 14, 2026

(54) HAIR TREATMENT COMPOSITIONS, KITS THEREOF, AND METHODS THEREOF

(71) Applicant: L'OREAL, Paris (FR)

(72) Inventors: Kazumitsu Kawakami, Westfield, NJ (US); Liliana Xavier, Mountainside, NJ (US)

(73) Assignee: L'OREAL, Paris (FR)

( * ) Notice: Subject to any disclaimer, the term of this patent is extended or adjusted under 35 U.S.C. 154(b) by 179 days.

(21) Appl. No.: 17/007,490

(22) Filed: Aug. 31, 2020

(65) Prior Publication Data

US 2022/0062133 A1 Mar. 3, 2022

(51) Int. Cl.

| | |
|---|---|
| ***A61K 8/41*** | (2006.01) |
| ***A61K 8/34*** | (2006.01) |
| ***A61K 8/73*** | (2006.01) |
| ***A61K 8/891*** | (2006.01) |
| ***A61K 8/92*** | (2006.01) |
| ***A61Q 5/12*** | (2006.01) |

(52) U.S. Cl.

CPC .............. *A61K 8/416* (2013.01); *A61K 8/345* (2013.01); *A61K 8/737* (2013.01); *A61K 8/891* (2013.01); *A61K 8/92* (2013.01); *A61Q 5/12* (2013.01); *A61K 2800/48* (2013.01); *A61K 2800/596* (2013.01)

(58) Field of Classification Search

None

See application file for complete search history.

(56) References Cited

U.S. PATENT DOCUMENTS

| | | | | |
|---|---|---|---|---|
| 10,137,073 | B2 | 11/2018 | De Lemos et al. | |
| 2002/0019547 | A1 | 2/2002 | Tuloup et al. | |
| 2002/0081271 | A1 | 6/2002 | Martin et al. | |
| 2002/0137795 | A1 | 9/2002 | Martin et al. | |
| 2003/0007987 | A1* | 1/2003 | Brieva | A61K 8/897 424/401 |
| 2003/0224060 | A1 | 12/2003 | Simonnet et al. | |
| 2007/0225360 | A1 | 9/2007 | Pinnell et al. | |
| 2008/0118449 | A1 | 5/2008 | Ronlan | |
| 2008/0160110 | A1 | 7/2008 | Kang et al. | |
| 2009/0286874 | A1 | 11/2009 | Pinnell et al. | |
| 2012/0282244 | A1* | 11/2012 | Maestro | A61K 36/82 424/729 |
| 2013/0061863 | A1* | 3/2013 | Grey | B65D 81/3205 132/200 |
| 2018/0185264 | A1* | 7/2018 | Holmes | A61K 8/8152 |
| 2018/0280270 | A1* | 10/2018 | Rughani | A61K 8/466 |
| 2018/0311140 | A1* | 11/2018 | Perner | A61K 8/44 |
| 2019/0201315 | A1* | 7/2019 | Gevgilili | A61K 8/463 |
| 2019/0350819 | A1 | 11/2019 | Hamersky et al. | |
| 2020/0069025 | A1 | 3/2020 | Ferebee Maher et al. | |
| 2020/0129405 | A1 | 4/2020 | Mitchell et al. | |

OTHER PUBLICATIONS

Preliminary Search Report and Written Opinion issued on Jun. 24, 2021 for corresponding French Application No. FR 2010415.
Database GNPD; Mintel; "Hair Mask", 2020 XP055816424.
Database GNPD; Mintel; "Thermo Protector", 2016 XP055816440.
Database GNPD; Mintel; "Conditioner", 2021 XP055816432.

* cited by examiner

*Primary Examiner* — Jennifer A Berrios
(74) *Attorney, Agent, or Firm* — POLSINELLI PC

(57) ABSTRACT

Hair treatment compositions, kits thereof, and methods of use thereof that provide enhanced color tone preservation. The hair treatment compositions typically include about 2 to about 10 wt. % of two or more cationic surfactants comprising a di-alkyl dimonium halide compound or salt thereof and a mono-alkyl trimonium halide compound or salt thereof; about 0.1 to about 10 wt. % of a thickening agent; about 10 wt. % or more of a fatty compound; about 0.1 to about 10 wt. % of a silicone; and water, wherein all weight percentages are based on the total weight of the hair treatment composition. Additionally, the hair treatment compositions are typically formulated to have a weight ratio of the total amount of the di-alkyl dimonium halide compound or salt thereof to the total amount of mono-alkyl trimonium halide compound or salt thereof that is about 1:10 to about 5:1.

17 Claims, No Drawings

HAIR TREATMENT COMPOSITIONS, KITS THEREOF, AND METHODS THEREOF

FIELD OF THE DISCLOSURE

The instant disclosure relates to the hair treatment compositions and kits thereof, and particularly to hair treatment compositions that provide enhanced color tone preservation. Additionally, aspects of the disclosure relate to methods for using such hair treatment compositions.

BACKGROUND

Many consumers desire to use cosmetic and care compositions that enhance the appearance of keratinous substrates such as hair, e.g., by changing the color, style, and/or shape of the hair, and/or by imparting various cosmetic properties to hair, such as shine and conditioning.

Consumers desire natural compositions for treating, caring for, and/or conditioning keratin fibers, such as hair. Such compositions can be difficult to produce as their materials must be sourced from natural and/or organic sources such as plants, while maintaining desirable performance properties.

In addition, consumers may expect some compositions to have certain properties, such as viscosity or rheology, to be recognized as a specific product—e.g., a hair conditioner, a body moisturizer, a face moisturizer, etc.—or to be convenient for dispensing and using. It is known to use conventional thickeners in such compositions in order to give the compositions a certain viscosity or rheology. However, chemicals and raw materials used in these conventional compositions may lack sustainable sourcing and therefore not comply with "green" manufacturing processes, which may make the compositions less desirable to consumers.

The present disclosure relates to hair treatment compositions, e.g. cosmetic compositions, that can treat, care for, and/or condition keratinous materials, wherein the compositions have desired cosmetic and composition properties. Without intending to be limiting, the compositions may impart one or more benefits such as suppleness, softness, moisturization, detangling, smoothness, discipline, and/or frizz control to keratinous materials.

SUMMARY OF THE DISCLOSURE

The instant disclosure relates to the hair treatment compositions and kits thereof, and particularly to hair treatment compositions that provide enhanced color tone preservation. Additionally, aspects of the disclosure relate to methods for using such hair treatment compositions.

The inventors discovered that certain combinations of ingredients in specific ratios enables hair treatment compositions that simultaneously provide enhanced conditioning properties and color tone preservation. Additionally, the color tone preservation was unexpectedly improved with hair that received bleaching agents (e.g., oxidizing agents) prior to coloring. While not intending to be limited by any specific theory, it is believed that the specific combination of cationic surfactants, silicone, and thickening agents in certain ratios contributes to the color tone preservation and the improved hair surface properties.

The hair treatment compositions may advantageously provide the foregoing benefits while not weighing down the hair. In some cases, the hair treatment compositions may provide a perceived change in the condition of the hair with one application of the hair treatment composition.

The hair treatment compositions typically include:

(a) about 2 to about 10 wt. % of two or more cationic surfactants comprising a di-alkyl dimonium halide compound or salt thereof and a mono-alkyl trimonium halide compound or salt thereof;
  wherein a weight ratio of the total amount of the di-alkyl dimonium halide compound or salt thereof to the total amount of mono-alkyl trimonium halide compound or salt thereof is about 1:10 to about 5:1,
(b) about 0.1 to about 10 wt. % of a thickening agent;
(c) about 10 wt. % or more of a fatty compound;
(d) about 0.1 to about 10 wt. % of a silicone; and
(e) water,
  wherein all weight percentages are based on the total weight of the hair treatment composition.

Preferably, the two or more cationic surfactants of the hair treatment compositions comprise about 0.5 to about 5 wt. % of a di-alkyl dimonium halide compound or salt thereof, such as dicetyldimonium chloride, and about 0.5 to about 5.5 wt. % of a mono-alkyl trimonium halide compound or salt thereof, such as behentrimonium chloride. In some cases, the two or more cationic surfactants comprise about 0.5 to about 2.5 wt. % of a di-alkyl dimonium halide compound or salt thereof, such as dicetyldimonium chloride, and about 2.5 to about 4.8 wt. % of a mono-alkyl trimonium halide compound or salt thereof, such as behentrimonium chloride. The weight ratio of the total amount of the di-alkyl dimonium halide compound or salt thereof to the total amount of mono-alkyl trimonium halide compound or salt thereof may be about 1:5 to about 1:1. In some cases, the hair treatment compositions include two or more cationic surfactants comprising dicetyldimonium chloride and behentrimonium chloride and the weight ratio is the total amount of dicetyldimonium chloride to total amount of behentrimonium chloride. Additionally or alternatively, the two or more cationic surfactants comprise dicetyldimonium chloride and behentrimonium chloride and may further include an additional cationic surfactant chosen from cetrimonium chloride, steartrimonium chloride, behentrimonium methosulfate, behenamidopropyltrimonium methosulfate, stearamidopropyltrimonium chloride, arachidtrimonium chloride, distearyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and mixtures thereof.

The treatment composition may include a thickening agent chosen from xanthan gum, guar gum, biosaccharide gum, cellulose, acacia seneca gum, sclerotium gum, agarose, pechtin, gellan gum, hyaluronic acid, and a mixture thereof. Preferably, thickening agent is hydroxypropyl guar.

The hair treatment composition may fatty compounds chosen from a fatty alcohol, a fatty ester, a fatty acid, a wax, an oil, a derivative thereof, and a mixture thereof. The fatty ester may be chosen from cetyl ester, purcellin oil (cetearyl octanoate), isopropyl myristate, isopropyl palmitate, $C_{12}$-$C_{15}$ alkyl benzoate, 2-ethylphenyl benzoate, isopropyl lanolate, hexyl laurate, diisopropyl adipate, isononyl isononanoate, oleyl erucate, 2-ethylhexyl palmitate, isostearyl isostearate, diisopropyl sebacate, octanoates, decanoates or ricinoleates of alcohols or polyalcohols, hydroxylated esters, and pentaerythritol esters, and a mixture thereof.

Suitable examples of fatty alcohols include those chosen from decyl alcohol, undecyl alcohol, dodecyl alcohol, myristyl alcohol, lauryl alcohol, cetyl alcohol, stearyl alcohol, cetearyl alcohol (cetyl alcohol and stearyl alcohol), isostearyl alcohol, isocetyl alcohol, behenyl alcohol, linalool, oleyl alcohol, cis-4-t-butylcyclohexanol, isotridecyl alcohol, myricyl alcohol, and a mixture thereof Non-limiting examples of waxes include, e.g., ceresin, paraffin, ozokerite, polyethylene waxes, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, acacia decurrents flower wax, vegetable waxes, carnauba, candelilla, ouricury or japan wax, or a mixture thereof.

The hair treatment composition may include about 0.5 to about 4.5 wt. % of bis-cetearyl amodimethicone. The silicone may further include dimethicone, amodimethicone, or a mixture thereof.

Additionally or alternatively, the hair treatment composition may include about 1 wt. % to about 10 wt. % of a polyol. The polyol may be chosen from ethylene glycol, propylene glycol, butylene glycol, hexylene glycol, pentylene glycol, diethylene glycol, dipropylene glycol, caprylyl glycol, 1,3 propanediol, glycerin, diglycerin, polyethylene glycols, and a mixture thereof.

According to another aspect, provided is a hair treatment kit. The hair treatment kits typically include a hair treatment composition according the instant disclosure and a shampoo.

In accordance with another aspect, provided is a method for treating hair. The methods for treating hair typically include:

(I) optionally, applying a shampoo to hair;

(II) optionally, rinsing the hair to remove at least a portion of the shampoo;

(III) applying a hair treatment composition comprising:

- (a) about 2 to about 10 wt. % of two or more cationic surfactants comprising a di-alkyl dimonium halide compound or salt thereof and a mono-alkyl trimonium halide compound or salt thereof, wherein a weight ratio of the total amount of the di-alkyl dimonium halide compound or salt thereof to the total amount of mono-alkyl trimonium halide compound or salt thereof is about 1:10 to about 5:1;
- (b) about 0.1 to about 10 wt. % of a thickening agent;
- (c) about 10 wt. % or more of a fatty compound;
- (d) about 0.1 to about 10 wt. % of a silicone; and
- (e) water, wherein all weight percentages are based on the total weight of the hair treatment composition; and (IV) optionally, rinsing the hair to remove at least a portion of the hair treatment composition.

DETAILED DESCRIPTION OF THE DISCLOSURE

Aspects of the disclosure relates to the hair treatment compositions and kits thereof, and particularly to hair treatment compositions that provide enhanced color tone preservation. The inventors discovered that certain combinations of ingredients in specific ratios enables hair treatment compositions that simultaneously provide enhanced conditioning properties and color tone preservation. Additionally, the color tone preservation was unexpectedly improved with hair that received bleaching agents (e.g., oxidizing agents) prior to coloring. While not intending to be limited by any specific theory, it is believed that the specific combination of cationic surfactants, silicone, and thickening agents in certain ratios contributes to the color tone preservation and the improved hair surface properties.

The hair treatment compositions typically include:

- (a) about 2 to about 10 wt. % of two or more cationic surfactants comprising a di-alkyl dimonium halide compound or salt thereof and a mono-alkyl trimonium halide compound or salt thereof,
  - wherein a weight ratio of the total amount of the di-alkyl dimonium halide compound or salt thereof to the total amount of mono-alkyl trimonium halide compound or salt thereof is about 1:10 to about 5:1,
- (b) about 0.1 to about 10 wt. % of a thickening agent;
- (c) about 10 wt. % or more of a fatty compound;
- (d) about 0.1 to about 10 wt. % of a silicone; and
- (e) water, wherein all weight percentages are based on the total weight of the hair treatment composition.

The hair treatment compositions may have a weight ratio of the total amount of the di-alkyl dimonium halide compound or salt thereof to the total amount of mono-alkyl trimonium halide compound or salt thereof of about 1:10 to about 5:1. In some cases, the weight ratio of the total amount of the di-alkyl dimonium halide compound or salt thereof to the total amount of mono-alkyl trimonium halide compound or salt thereof is about 1:9 to about 5:1, about 1:8 to about 5:1, about 1:7 to about 5:1, about 1:6 to about 5:1, about 1:5 to about 5:1, about 1:4 to about 5:1, about 1:10 to about 5:1, about 1:10 to about 4:1, about 1:10 to about 3:1, about 1:10 to about 2:1, about 1:10 to about 1:1, including all ranges and subranges therebetween (e.g., about 1:8 to about 1:3, about 1:7 to about 1:2, about 1:6 to about 1:2, about 1:5 to about 1:1, etc.).

Suitable components, such as those listed below, may be included or excluded from the formulations for the hair treatment compositions depending on the specific combination of other components, the form of the hair treatment compositions, and/or the use of the formulation (e.g., a lotion, gel, cream, spray, etc.).

Cationic Surfactants

The hair treatment composition include two or more cationic surfactants comprising a di-alkyl dimonium halide compound or salt thereof and a mono-alkyl trimonium halide compound or salt thereof. The amount of cationic surfactant(s) may be from about 2 to about 10 wt. % of the total weight of the hair treatment composition. In some instances, the cationic surfactant(s) are in an amount ranging from about 2 to about 9 wt. %, about 2 to about 8 wt. %, about 2 to about 7 wt. %, about 2 to about 6 wt. %, about 2 to about 5 wt. %, about 2 to about 4 wt. %, about 2 to about 3 wt. %; about 3 to about 9 wt. %, about 3 to about 8 wt. %, about 3 to about 7 wt. %, about 3 to about 6 wt. %, about 3 to about 5 wt. %, about 3 to about 4 wt. %; about 4 to about 9 wt. %, about 4 to about 8 wt. %, about 4 to about 7 wt. %, about 4 to about 6 wt. %, about 4 to about 5 wt. %; about 5 to about 9 wt. %, about 5 to about 8 wt. %, about 5 to about 7 wt. %, or about 5 to about 6 wt. %, including ranges and sub-ranges therebetween, based on the total weight of the hair treatment composition.

Preferably, the two or more cationic surfactants comprise dicetyldimonium chloride and behentrimonium chloride. Additionally or alternatively, the two or more cationic surfactants comprise about 0.5 to about 5 wt. % of dicetyldimonium chloride and about 0.5 to about 5.5 wt. % of behentrimonium chloride. For example, the amount of dicetyldimonium chloride may be about 0.5 to about 5 wt. %, about 0.5 to about 4.5 wt. %, about 0.5 to about 4 wt. %, about 0.5 to about 3.5 wt. %, about 0.5 to about 3 wt. %, about 0.5 to about 2.5 wt. %, about 0.5 to about 2 wt. %, about 0.5 to about 1.5 wt. %; about 1 to about 5 wt. %, about 1 to about 4.5 wt. %, about 1 to about 4 wt. %, about 1 to about 3.5 wt. %, about 1 to about 3 wt. %, about 1 to about 2.5 wt. %, about 1 to about 2 wt. %; about 1.5 to about 5 wt. %, about 1.5 to about 4.5 wt. %, about 1.5 to about 4 wt. %, about 1.5 to about 3.5 wt. %, about 1.5 to about 3 wt. %, about 1.5 to about 2.5 wt. %, about 1.5 to about 2 wt. %; about 2 to about 5 wt. %, about 2 to about 4.5 wt. %, about 2 to about 4 wt. %, about 2 to about 3.5 wt. %, about 2 to about 3 wt. %; about 2.5 to about 5 wt. %, about 2.5 to about 4.5 wt. %, about 2.5 to about 4 wt. %, about 2.5 to about 3.5 wt. %; about 3 to about 5 wt. %, about 3 to about 4.5 wt. %, about 3 to about 4 wt. %; about 3.5 to about 5 wt. %, about 3.5 to about 4.5 wt. %, including ranges and sub-ranges therebetween, based on the total weight of the hair treatment composition.

The amount of behentrimonium chloride may be about 0.5 to about 5.5 wt. %, about 0.5 to about 5 wt. %, about 0.5 to about 4.5 wt. %, about 0.5 to about 4 wt. %, about 0.5 to about 3.5 wt. %, about 0.5 to about 3 wt. %, about 0.5 to about 2.5 wt. %, about 0.5 to about 2 wt. %, about 0.5 to about 1.5 wt. %; about 1 to about 5.5 wt. %, about 1 to about 5 wt. %, about 1 to about 4.5 wt. %, about 1 to about 4 wt. %, about 1 to about 3.5 wt. %, about 1 to about 3 wt. %, about 1 to about 2.5 wt. %, about 1 to about 2 wt. %; about 1.5 to about 5.5 wt. %, about 1.5 to about 5 wt. %, about 1.5 to about 4.5 wt. %, about 1.5 to about 4 wt. %, about 1.5 to about 3.5 wt. %, about 1.5 to about 3 wt. %, about 1.5 to about 2.5 wt. %, about 1.5 to about 2 wt. %; about 2 to about 5.5 wt. %, about 2 to about 5 wt. %, about 2 to about 4.5 wt. %, about 2 to about 4 wt. %, about 2 to about 3.5 wt. %, about 2 to about 3 wt. %; about 2.5 to about 5.5 wt. %, about 2.5 to about 5 wt. %, about 2.5 to about 4.5 wt. %, about 2.5 to about 4 wt. %, about 2.5 to about 3.5 wt. %; about 3 to about 5.5 wt. %, about 3 to about 5 wt. %, about 3 to about 4.5 wt. %, about 3 to about 4 wt. %; about 3.5 to about 5.5 wt. %, about 3.5 to about 5 wt. %, about 3.5 to about 4.5 wt. %, about 4 to about 5.5 wt. %, about 4 to about 5 wt. %; about 4.5 to about 5.5 wt. %, including ranges and sub-ranges therebetween, based on the total weight of the hair treatment composition.

The hair treatment compositions may have a weight ratio of the total amount of the di-alkyl dimonium halide compound or salt thereof to the total amount of mono-alkyl trimonium halide compound or salt thereof of about 1:10 to about 5:1. In some cases, the weight ratio of the dicetyldimonium chloride to the behentrimonium chloride is about 1:9 to about 5:1, about 1:8 to about 5:1, about 1:7 to about 5:1, about 1:6 to about 5:1, about 1:5 to about 5:1, about 1:4 to about 5:1, about 1:10 to about 5:1, about 1:10 to about 4:1, about 1:10 to about 3:1, about 1:10 to about 2:1, about 1:10 to about 1:1, including all ranges and subranges therebetween (e.g., about 1:8 to about 1:3, about 1:7 to about 1:2, about 1:6 to about 1:2, about 1:5 to about 1:1, etc.). In some cases, the hair treatment compositions include two or more surfactants comprising dicetyldimonium chloride and behentrimonium chloride and the weight ratio is the total amount of dicetyldimonium chloride to total amount of behentrimonium chloride.

The cationic surfactant(s) may be chosen from optionally polyoxyalkylenated, primary, secondary or tertiary fatty amines, or salts thereof, and quaternary ammonium salts, and mixtures thereof. In some cases, it is useful to use salts such as chloride salts of the quaternary ammonium compounds.

Suitable examples of cationic surfactants are behentrimonium chloride, cetrimonium chloride, steartrimonium chloride, behentrimonium methosulfate, behenamidopropyltrimonium methosulfate, stearamidopropyltrimonium chloride, arachidtrimonium chloride, dicetyldimonium chloride, distearyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, and arachidamidoethyidimethylamine.

Additional, non-limiting examples of cationic surfactants include palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, behenalkonium chloride, benzethonium chloride, cetylpyridinium chloride, lauralkonium chloride, cetalkonium chloride, cetrimonium bromide, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, diethanolammonium POE (10) oletyl ether phosphate, diethanolammonium POE (3) oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, stearalkonium bentonite, stearalkoniumhectonite, stearyl trihydroxyethyl propylenediamine dihydrofluoride, tallowtrimonium chloride, hexadecyltrimethyl ammonium bromide, and mixtures thereof.

The fatty amines generally comprise at least one $C_8$-$C_{30}$ hydrocarbon-based chain. Quaternary ammonium salts include those corresponding to the following general formula:

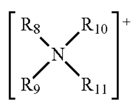

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms and preferably from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyl, $C_1$-$C_{30}$ alkoxy, polyoxy ($C_2$-$C_6$)alkylene, $C_1$-$C_{30}$ alkylamide, ($C_{12}$-$C_{22}$)alkylamido ($C_2$-$C_6$) alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts having a structure in accordance with the above general formula (III), those that are preferred are, on the one hand, tetraalkylammonium salts, for instance dialkyldimethylammonium or alkyltrimethylammonium salts in which the alkyl group contains approximately from 12 to 22 carbon atoms, such as behenyltrimethylammonium, distearyldimethylammonium, cetyltrimethylammonium or benzyldimethylstearylammonium salts, or, on the other hand, oleocetyldimethylhydroxyethylammonium salts, palmitylamidopropyltrimethylammonium salts, stearamidopropyltrimethylammonium salts and stearamidopropyldimethylcetearylammonium salts.

Examples of quaternary ammonium salt of imidazoline, which may be incorporated in certain instances, include those having a structure according to the general formula provided below:

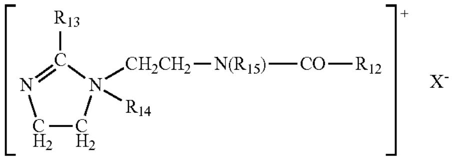

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, X is an anion chosen from the group of halides, phosphates, acetates, lactates, alkyl sulfates, alkyl- or alkylarylsulfonates in which the alkyl and aryl groups preferably comprise, respectively, from 1 to 20 carbon atoms and from 6 to 30 carbon atoms. $R_{12}$ and $R_{13}$ preferably denote a mixture of alkenyl or alkyl groups containing from 12 to 21 carbon atoms, derived for example from tallow fatty acids, $R_{14}$ preferably denotes a methyl group, and $R_{15}$ preferably denotes a hydrogen atom. Such a product is sold, for example, under the name REWOQUAT W 75 by the company Rewo.

Examples of quaternary diammonium or triammonium salt, which may be incorporated in certain instances, include those having a structure in accordance with the following general formula:

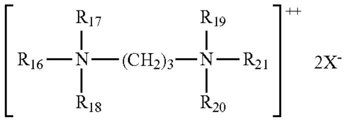

in which $R_{16}$ denotes an alkyl radical comprising approximately from 16 to 30 carbon atoms, which is optionally hydroxylated and/or interrupted with one or more oxygen atoms; $R_{17}$ is chosen from hydrogen or an alkyl radical comprising from 1 to 4 carbon atoms or a group $(R_{16a})(R_{17a})(R_{18a})N—(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms; and X is an anion chosen from the group of halides, acetates, phosphates, nitrates and methyl sulfates. Such compounds are, for example, Finquat CT-P, sold by the company Finetex (Quaternium 89), and Finquat CT, sold by the company Finetex (Quaternium 75), Examples of cationic/cationizable surfactants, which may be incorporated in certain instances, include those having a structure in accordance with the general formula provided below:

R4-A-R5—B wherein R4 is a saturated or unsaturated, straight or branched alkyl chain with 8 to 24 carbon atoms, $R_5$ is a straight or branched alkyl chain with 1 to 4 carbon atoms, A is selected from:

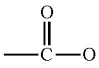

and

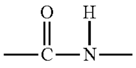

and B is selected from:

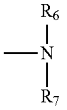

wherein $R_6$ and $R_7$ are the same or different and are H or an alkyl chain with 1 to 4 carbon atoms, hydroxyl alkyl chain with 1 to 4 carbon atoms and di hydroxyl alkyl chain with 2 to 4 carbon atoms,

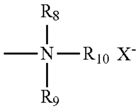

$R_8$ and $R_9$ are the same or different, an alkyl chain with 1 to 4 carbon atoms, hydroxyl alkyl chain with 1 to 4 carbon atoms and di hydroxyl alkyl chain with 2 to 4 carbon atoms, $R_{10}$ is an alkyl chain with 1 to 4 carbon atoms, hydroxyl alkyl chain with 1 to 4 carbon atoms or di hydroxyl alkyl chain with 2 to 4 carbon atoms.

In some instances, $R_4$ is saturated or unsaturated, straight or branched alkyl chain with 10 to 24 carbon atoms, more preferably 12 to 22 carbon atoms and $R_5$ is straight or branched alkyl group with 1 to 4 carbon atoms, and A, B, $R_6$ to $R_{10}$ are same as above.

Non-limiting suitable examples are stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl dimethylamine, stearamidopropyl diethylami ne, stearamidopropyldibutylamine, stearamidopropyl butylamine, stearamidopropyl dipr opylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, and dicocoylethylhydroxyethylmonium methosulfate.

Cationizable surfactants may be chosen from fatty alkylamines, preferably, fatty dialkylamines. Non-limiting examples include dimethyl lauramine, dimethyl behenamine, dimethyl cocamine, dimethyl myristamine, dimethyl palmitamine, dimethyl stearamine, dimethyl tallowamine, dimethyl soyamine, and mixtures thereof.

Fatty dialkylamines include fatty amidoamine compounds, their salts, and mixtures thereof. Non-limiting examples include oleamidopropyl dimethylamine, linoleamidopropyl dimethylamine, isostearamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, and palmitamidopropyl dimethylamine.

Non-polymeric, mono-, di-, and/or tri-carboxylic acids may be used to "neutralize" the fatty dialkylamines. In some cases, the one or more non-polymeric, mono-, di-, and/or tri-carboxylic acids include at least one dicarboxylic acid. Non-limiting examples include lactic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, benzoic acid, and mixtures thereof. In particular, lactic acid or tartaric acid or mixtures thereof are useful, especially in combination with fatty dimethylamines such as, for example, stearamidopropyl dimethylamine.

In an embodiment, the hair treatment composition may be formulated with a cationic surfactant chosen from dicetyldimonium chloride, behentrimonium chloride, cetrimonium chloride, behentrimonium methosulfate, or mixtures thereof.

The hair treatment composition may be formulated such that the two or more cationic surfactants are associated with the same or different balancing anionic ions. For example, at least one of the two or more cationic surfactants may have a chloride ion and/or a sulfate ion. In some instances, the two or more cationic surfactants comprise cetrimonium chloride and one or both of behentrimonium methosulfate and behentrimonium chloride. In further instances, the two or more cationic surfactants comprise behentrimonium chloride and one or both of behentrimonium methosulfate and cetrimonium chloride.

In yet another instance, the cationic surfactant(s) is chosen from cetrimonium chloride, stearimonium chloride, behentrimonium methosulfate, behenamidopropyltrimonium methosulfate, stearamidopropyltrimonium chloride, arachidtrimonium chloride, distearyldimonium chloride, tricetylmonium chloride, oleamidopropyl dimethylamine, linoleamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and a mixture thereof.

Thickening Agent(s)

The hair treatment compositions described include a thickening agent in an amount that can vary but is typically from about 0.1 to about 10 wt. %, based on the total weight of the hair treatment composition. In some instances, the amount of fatty compounds present in the hair treatment compositions is about 0.1 to about 9 wt. %, about 0.1 to about 8 wt. %, about 0.1 to about 7 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.5 to about 10 wt. %, about 0.5 to about 9 wt. %, about 0.5 to about 8 wt. %, about 0.5 to about 7 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 1 to about 10 wt. %, about 1 to about 9 wt. %, about 1 to about 8 wt. %, about 1 to about 7 wt. %, about 1 to about 6 wt. %, about 1 to about 5 wt. %, about 1 to about 4 wt. %, about 1 to about 3 wt. %; about 2 to about 10 wt. %, about 2 to about 9 wt. %, about 2 to about 8 wt. %, about 2 to about 7 wt. %, about 2 to about 6 wt. %, about 2 to about 5 wt. %; about 3 to about 10 wt. %, about 3 to about 9 wt. %, about 3 to about 8 wt. %, about 3 to about 7 wt. %, about 3 to about 6 wt. %, about 3 to about 5 wt. %; about 4 to about 10 wt. %, about 4 to about 9 wt. %, about 4 to about 8 wt. % about 4 to about 7 wt. %, about 4 to about 6 wt. %, about 4 to about 5 wt. %; about 5 to about 10 wt. %, about 5 to about 9 wt. %, about 5 to about 8 wt. %, about 5 to about 7 wt. %, or about 5 to about 6 wt. %, including all ranges and sub-ranges therebetween, based on the total weight of the hair treatment composition.

The thickening agent(s) may be chosen from polysaccharides such as celluloses and gums. Suitable examples of thickening agent(s) are xanthan gum, guar gum, biosaccharide gum, cellulose, acacia seneca gum, sclerotium gum, agarose, pectin, gellan gum, hyaluronic acid. Additionally, the one or more thickening agents may include polymeric thickening agents selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer. In some cases, the thickening agent(s) includes ammonium polyacryloyldimethyl taurate and/or sodium polyacrylate. Suitable thickening agents may be found in U.S. patent application Ser. No. 16/731,654, which is incorporated herein, in its entirety for all purposes.

Preferably, the thickening agent is chosen from xanthan gum, guar gum, hydroxypropyl guar, biosaccharide gum, cellulose, acacia seneca gum, sclerotium gum, agarose, pectin, gellan gum, hyaluronic acid, and a mixture thereof. In at least one instance, the thickening agent is hydroxypropyl guar.

Many thickening agents are water-soluble, and increase the viscosity of water or form an aqueous gel when the hair treatment composition of the invention is dispersed/dissolved in water. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water.

Particular types of thickening agents that may be mentioned include the following:

One or more thickening agents can optionally be included in the hair treatment compositions of the instant disclosure. Thickening agents may be referred to as "thickeners" or "viscosity modifying agents." Thickening agents are typically included to increase the viscosity of the hair treatment compositions. Nonetheless, in some instances, certain thickening agents provide additional, surprising benefits to the hair treatment compositions. Non-limiting examples of thickening agents include polyacrylate crosspolymers or crosslinked polyacrylate polymers, cationic acrylate copolymers, anionic acrylic or carboxylic acid polymers, polyacrylamide polymers, polysaccharides such as cellulose derivatives, gums, polyquaterniums, vinylpyrrolidone homopolymers/copolymers, C8-24 hydroxyl substituted aliphatic acid, C8-24 conjugated aliphatic acid, sugar fatty esters, polyglyceryl esters, and a mixture thereof. Particular types of thickening agents that may be mentioned include the following:

Carboxylic Acid or Carboxylate Based Homopolymer or Co-Polymer, which can be Linear or Crosslinked:

These polymers contain one or more monomers derived from acrylic acid, substituted acrylic acids, and salts and esters of these acrylic acids (acrylates) and the substituted acrylic acids. Commercially available polymers include those sold under the trade names CARBOPOL, ACRYSOL, POLYGEL, SOKALAN, CARBOPOL ULTREZ, and POLYGEL. Examples of commercially available carboxylic acid polymers include the carbomers, which are homopolymers of acrylic acid crosslinked with allyl ethers of sucrose or pentaerytritol. The carbomers are available as the CARBOPOL 900 series from B.F. Goodrich (e.g., CARBOPOL 954). In addition, other suitable carboxylic acid polymeric agents include ULTREZ 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as CARBOPOL 1342, CARBOPOL 1382, PEMULEN TR-1, and PEMULEN TR-2, from B.F. Goodrich.

Other suitable carboxylic acid or carboxylate polymeric agents include copolymers of acrylic acid and alkyl C5-C10 acrylate, copolymers of acrylic acid and maleic anhydride, and polyacrylate crosspolymer-6. Polyacrylate Crosspolymer-6 is aviable in the raw material known as SEPIMAX ZEN from Seppic.

Another suitable carboxylic acid or carboxylate polymeric agent includes acrylamidopropyltrimonium chloride/acrylates copolymer, a cationic acrylates copolymer (or a quaternary ammonium compound), available as a raw maerial known under the tradename of SIMULQUAT HC 305 from Seppic.

In certain embodiments, the carboxylic acid or carboxylate polymer thickening agents useful herein are those selected from carbomers, acrylates/C10-C30 alkyl acrylate crosspolymers, polyacrylate crosspolymer-6, acrylamidopropyltrimonium chloride/acrylates copolymer, and mixtures thereof.

Polyquaternium Compounds:

Non-limiting examples, include polyquaternium-1, polyquaternium-2, polyquaternium-3, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-21, polyquaternium-22, polyquaternium-23, polyquaternium-24, polyquaternium-25, polyquaternium-26, polyquaternium-27, polyquaternium-28, polyquaternium-29, polyquaternium-30, polyquaternium-40, polyquaternium-41, polyquaternium-42, polyquaternium-43, polyquaternium-44, polyquaternium-45, polyquaternium-46, polyquaternium-47, polyquaternium-48, polyquaternium-49, polyquaternium-50, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-61, polyquaternium-62, polyquaternium-63, polyquaternium-64, polyquaternium-65, polyquaternium-66, polyquaternium-67, etc. In some cases, preferred polyquaternium compounds include polyquaternium-10, polyquaternium-11, polyquaternium-67, and a mixture thereof.

Celluloses:

Non-limiting examples of celluloses include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. In some instances, the cellulose is selected from water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt). Furthermore, in some instance, the cellulose is preferably hydroxypropylcellulose (HPC).

Polyvinylpyrrolidone (PVP) and Co-Polymers:

Non-limiting examples include Polyvinylpyrrolidone (PVP), Polyvinylpyrrolidone (PVP)/vinyl acetate copolymer (PVP/VA copolymer), polyvinylpyrrolidone (PVP)/eicosene copolymer, PVP/hexadecene copolymer, etc. Commercially available polyvinylpyrrolidone includes LUVISKOL K30, K85, K90 available from BASF. Commerically available copolymers of vinylpyrrolidone and vinylacetate include LUVISKOL VA37, VA64 available from BASF; copolymers of vinylpyrrolidone, methacrylamide, and vinylimidazole (INCI: VP/Methacrylamide/Vinyl Imidazole Copolymer) is commercially available as LUVISET from BASF. In some instances, PVP and PVP/VA copolymer are preferred.

Sucrose Esters:

Non-limiting examples include sucrose palmitate, sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose pentaoleate, sucrose hexaoleate, sucrose heptaoleate or sucrose octooleate, and mixed esters, such as sucrose palmitate/stearate, and mixtures thereof.

Polyglyceryl Esters:

Non-limiting polyglycerol esters of fatty acids (polyglyceryl esters) include those of the following formula:

$$R^1\text{—}(OCH_2\text{-}\underset{|}{\overset{OR^2}{CH}}\text{-}CH_2O)_n\text{—}R_3$$

wherein n is from 2 to 20 or from 2 to 10 or from 2 to 5, or is 2, 3, 4, 5, 6, 7, 8, 9, or 10, and $R_1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R_3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and mixtures thereof.

Gums:

Non-limiting examples of gums include gum arabic, tragacanth gum, karaya gum, guar gum, gellan gum, tara gum, locust bean gum, tamarind gum, xanthan gum, locust bean gum, Seneca gum, sclerotium gum, gellan gum, etc.

Fatty Compound(s)

The hair treatment compositions include one or more fatty compound(s) in amount that may vary, but is typically about 10 wt. % or more, based on the total weight of the hair treatment compositions. In some instances, the amount of fatty compound(s) in the hair treatment composition may be 11 wt. % or more, 12 wt. % or more, 13 wt. % or more, 14 wt. % or more, 15 wt. % or more, 20 wt. % or more, 25 wt. % or more, or 30 wt. % or more, based on the total weight of the hair treatment composition.

Additionally or alternatively, the hair treatment compositions may have an amount of fatty compound(s) of about 10 to about 80 wt. %, about 10 to about 70 wt. %, about 10 to about 60 wt. %, about 10 to about 50 wt. %, about 10 to about 40 wt. %, about 10 to about 30 wt. %, about 10 to about 20 wt. %, about 10 to about 18 wt. %, about 10 to about 16 wt. %, about 10 to about 14 wt. %, about 10 to about 12 wt. %; about 12 to about 80 wt. %, about 12 to about 70 wt. %, about 12 to about 60 wt. %, about 12 to about 50 wt. %, about 12 to about 40 wt. %, about 12 to about 30 wt. %, about 12 to about 20 wt. %, about 10 to about 18 wt. %, about 12 to about 16 wt. %, about 12 to about 14 wt. %; about 14 to about 80 wt. %, about 14 to about 70 wt. %, about 14 to about 60 wt. %, about 14 to about 50 wt. %, about 14 to about 40 wt. %, about 14 to about 30 wt. %, about 14 to about 20 wt. %, about 14 to about 18 wt. %; about 16 to about 80 wt. %, about 16 to about 70 wt. %, about 16 to about 60 wt. %, about 16 to about 50 wt. %, about 16 to about 40 wt. %, about 16 to about 30 wt. %, about 16 to about 20 wt. %; about 18 to about 80 wt. %, about 18 to about 70 wt. %, about 18 to about 60 wt. %, about 18 to about 50 wt. %, about 18 to about 40 wt. %, about 18 to about 30 wt. %, about 18 to about 25 wt. %; about 20 to about 80 wt. %, about 20 to about 70 wt. %, about 20 to about 60 wt. %, about 20 to about 50 wt. %, about 20 to about 40 wt. %, about 20 to about 30 wt. %, about 20 to about 25 wt. %; about 25 to about 80 wt. %, about 25 to about 70 wt. %, about 25 to about 60 wt. %, about 25 to about 50 wt. %, about 25 to about 40 wt. %, or about 25 to about 30 wt. %, including ranges and subranges thereof, based on the total weight of the hair treatment compositions.

Examples of fatty compound(s) that may be incorporated into the hair treatment composition include fatty alcohol, a fatty ester, a fatty ether, a fatty acid, a wax, an oil, a derivative thereof, and a mixture thereof. Additional examples of fatty compounds that are worth mentioning include oils, mineral oil, alkanes (paraffins), fatty alcohol derivatives, fatty acid derivatives, esters of fatty alcohols, hydroxy-substituted fatty acids, waxes, triglyceride compounds, lanolin, and a mixture thereof.

The fatty compounds may preferably be chosen from a fatty alcohol, a fatty ester, a fatty acid, a wax, an oil, a derivative thereof, and a mixture thereof. The fatty ester may be chosen from cetyl ester, purcellin oil (cetearyl octanoate), isopropyl myristate, isopropyl palmitate, C12-C15 alkyl benzoate, 2-ethylphenyl benzoate, isopropyl lanolate, hexyl laurate, diisopropyl adipate, isononyl isononanoate, oleyl erucate, 2-ethylhexyl palmitate, isostearyl isostearate, diisopropyl sebacate, octanoates, decanoates or ricinoleates of alcohols or polyalcohols, hydroxylated esters, and pentaerythritol esters, and a mixture thereof. Suitable examples of fatty alcohols include those chosen from decyl alcohol, undecyl alcohol, dodecyl alcohol, myristyl alcohol, lauryl alcohol, cetyl alcohol, stearyl alcohol, cetearyl alcohol (cetyl alcohol and stearyl alcohol), isostearyl alcohol, isocetyl alcohol, behenyl alcohol, linalool, oleyl alcohol, cis-4-t-butylcyclohexanol, isotridecyl alcohol, myricyl alcohol, and a mixture thereof. Non-limiting examples of waxes include, e.g., ceresin, paraffin, ozokerite, polyethylene waxes, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, acacia decurrents flower wax, vegetable waxes, carnauba, candelilla, ouricury or japan wax, or a mixture thereof.

Further discussion of fatty compounds that may, in some cases, be suitably included in the hair treatment compositions are discussed below.

Fatty Ester(s)

The hair treatment compositions may include one or more fatty compound(s) that is a fatty ester. For example, the fatty compound(s) may be chosen from dialkyl carbonates of formula: $R_1O(C{=}O)R_2$, wherein $R_1$ and $R_2$ are independently linear or branched, saturated or unsaturated alkyl chains having 1 to 30 carbon atoms, or having 2 to 28 carbon atoms, or having 4 to 25 carbon atoms, or having 6 to 22 carbon atoms, preferably one or more fatty carbonates selected from C14-15 dialkyl carbonate, dicaprylyl carbonate, diethyl carbonate, dihexyl carbonate, diethylhexyl carbonate, dimethoxyphenyl phenyloxoethyl ethylcarbonate, dimethyl carbonate, dipropyl carbonate, dipropylheptyl carbonate, dioctyl carbonate, and a mixture thereof.

Additionally or alternatively, the fatty ester chosen from cetyl ester, purcellin oil (cetearyl octanoate), isopropyl myristate, isopropyl palmitate, $C_{12}$-$C_{15}$ alkyl benzoate, 2-ethylphenyl benzoate, isopropyl lanolate, hexyl laurate, diisopropyl adipate, isononyl isononanoate, oleyl erucate, 2-ethylhexyl palmitate, isostearyl isostearate, diisopropyl sebacate, octanoates, decanoates or ricinoleates of alcohols or polyalcohols, hydroxylated esters, dicaprylyl carbonate, pentaerythritol esters, and a mixture thereof. Other fatty esters worth mentioning include polyglyceryl-10 oleate, polyglyceryl-10 dioleate, polyglyceryl-6 stearate, polyglyceryl-6 distearate, polyglyceryl-10 stearate, polyglyceryl-10 distearate, polyglyceryl-8 dipalmitate, polyglyceryl-10 dipalmitate, polyglyceryl-10 behenate, and polyglyceryl-12 trilaurate.

Fatty Alcohol(s)

Suitable fatty alcohols, if present, include those having a fatty group with a carbon chain of greater than 8 carbon atoms, 8 to 50 carbon atoms, 8 to 40 carbon atoms, 8 to 30 carbon atoms, 8 to 22 carbon atoms, 12 to 22 carbon atoms, or 12 to 18 carbon atoms, including all ranges and subranges therebetween. In some instances, the fatty group of the fatty alcohols has a carbon chain of 10 to 20 carbon atoms or 10 to 18 carbon atoms. The fatty alcohols may be chosen from polyethylene glycol ethers, such as those having a fatty alcohol group with a carbon chain of 12 to 16 or 12 to 14 carbon atoms.

The fatty alcohol portion is preferably hydrogenated (for example, stearyl, lauryl, cetyl, cetearyl); however, the fatty alcohol may contain one or more double bonds (for example, oleyl). Non-limiting examples of fatty alcohols include decyl alcohol, undecyl alcohol, dodecyl alcohol, myristyl alcohol, lauryl alcohol, cetyl alcohol, stearyl alcohol, cetearyl alcohol (cetyl alcohol and stearyl alcohol), isostearyl alcohol, isocetyl alcohol, behenyl alcohol, linalool, oleyl alcohol, cis-4-t-butylcyclohexanol, isotridecyl alcohol, myricyl alcohol, and a mixture thereof. In some cases, the fatty alcohols comprise at least one of or may be chosen from myristyl alcohol, lauryl alcohol, cetyl alcohol, stearyl alcohol, cetearyl alcohol, isostearyl alcohol, oleyl alcohol, isotridecyl alcohol, and a mixture thereof.

The fatty alcohol may be saturated or unsaturated. Exemplary saturated liquid fatty alcohols may be branched and optionally contain in their structure at least one aromatic or non-aromatic ring. In some instances, however, the fatty alcohols are acyclic. Non-limiting examples of liquid saturated fatty alcohols include octyldodecanol, isostearyl alcohol, and 2-hexyldecanol.

Exemplary unsaturated liquid fatty alcohol may include in their structure at least one double or triple bond. For example, the fatty alcohols may include several double bonds (such as 2 or 3 double bond), which may be conjugated or non-conjugated. The unsaturated fatty alcohols can be linear or branched and may be acyclic or include in their structure at least one aromatic or non-aromatic ring. Liquid unsaturated fatty alcohols may include or be chosen from oleyl alcohol, linoleyl alcohol, linolenyl alcohol and undecylenyl alcohol.

The fatty alcohols may be alkoxylated fatty alcohols, e.g., having about 1 to about 100 moles of an alkylene oxide per mole of alkoxylated fatty alcohol. For example, the alkoxylated fatty alcohols may be alkoxylated with about 1 to about 80 moles, about 2 to about 50, about 5 to about 45 moles, about 10 to about 40 moles, or 15 to about 35 mores, including all ranges and subranges therebetween, of an alkylene oxide per mole of alkoxylated fatty alcohol.

As examples of alkoxylated fatty alcohols, steareth (for example, steareth-2, steareth-20, and steareth-21), laureth (for example, laureth-4, and laureth-12), ceteth (for example, ceteth-10 and ceteth-20) and ceteareth (for example, ceteareth-2, ceteareth-10, and ceteareth-20) are mentioned. In at least one instance, the one or more alkoxylated fatty alcohols include steareth-20. In some instances, the one or more alkoxylated fatty alcohols may be exclusively steareth-20.

Additional fatty alcohol derivatives that may, optionally be suitable include methyl stearyl ether; 2-ethylhexyl dodecyl ether; stearyl acetate; cetyl propionate; the ceteth series of compounds, such as ceteth-1 through ceteth-45, which are ethylene glycol ethers of cetyl alcochol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Fatty Ether(s)

The fatty compounds may be chosen from fatty ethers. For example, the hair treatment composition may include olyoxyethylene cetyl/stearyl ether, polyoxyethylene cholesterol ether, polyoxyethylene laurate or dilaurate, polyoxyethylene stearate or distearate, polyoxyethylene lauryl or stearyl ether, dicaprylyl ether, dicetyl ether distearyl ether, or a mixture thereof. Non-limiting examples of suitable polyoxyethylene fatty ethers include, but are not limited to, polyoxyethylene cetyl/stearyl ether, polyoxyethylene cholesterol ether, polyoxyethylene laurate or dilaurate, polyoxyethylene stearate or distearate, polyoxyethylene lauryl or stearyl ether, and mixtures thereof, wherein the polyoxyethylene head group ranges from about 2 to about 100 groups. In certain embodiments, the polyoxyethylene fatty ethers include polyoxyethylene stearyl ether, polyoxyethylene myristyl ether, polyoxyethylene lauryl ether having from about 3 to about 10 oxyethylene units and mixtures thereof.

Fatty Acid(s)

In some instances, the fatty compounds may be chosen from fatty acids, fatty acid derivatives, esters of fatty acids, hydroxyl-substituted fatty acids, and alkoxylated fatty acids. The fatty acids may be straight or branched chain acids and/or may be saturated or unsaturated. Non-limiting examples of fatty acids include diacids, triacids, and other multiple acids as well as salts of these fatty acids. For example, the fatty acid may optionally include or be chosen from lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Non-limiting examples of polyglycerol esters of fatty acids include those of the following formula:

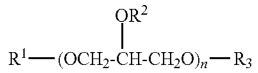

wherein the average value of n is about 3 and $R^1$, $R^2$ and $R^3$ each may independently be a fatty acid moiety or hydrogen, provided that at least one of $R_1$, $R_2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Non-limiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

Wax(es)

The fatty compounds may, in some instances, include or be chosen from one or more waxes. Non-limiting examples of waxes in this category include for example, synthetic wax, ceresin, paraffin, ozokerite, polyethylene waxes, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, acacia decurrents flower wax, vegetable waxes (such as sunflower seed (*Helianthus annuus*), carnauba, candelilla, ouricury or japan wax or cork fibre or sugarcane waxes), or a mixture thereof.

Oil(s)

In some instances, the fatty compounds may include or be chosen from one or more oil(s). Suitable oils include, but are not limited to, natural oils, such as coconut oil; hydrocarbons, such as mineral oil and hydrogenated polyisobutene; fatty alcohols, such as octyldodecanol; esters, such as $C_{12}$-$C_{15}$ alkyl benzoate; diesters, such as propylene dipelarganate; and triesters, such as glyceryl trioctanoate. Non-limiting examples of oils that may, optionally, be included in the hair treatment compositions include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isododecanol, polyglyceryl-3-diisostearate, castor oil, lanolin and lanolin derivatives, triisocetyl citrate, sorbitan sesquioleate, $C_{10}$-$C_{18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

Silicone(s)

The hair treatment composition includes silicone(s) typically in an amount ranging from about 0.1 to about 10 wt. %, based on the total weight of the hair treatment composition. For example, the amount of silicone(s) present in the hair treatment composition may be about 0.1 to about 9 wt. %, about 0.1 to about 8 wt. %, about 0.1 to about 7 wt. %, about 0.1 to about 6.5 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.5 to about 10 wt. %, about 0.5 to about 9 wt. %, about 0.5 to about 8 wt. %, about 0.5 to about 7 wt. %, about 0.5 to about 6.5 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 1 to about 10 wt. %, about 1 to about 9 wt. %, about 1 to about 8 wt. %, about 1 to about 7 wt. %, about 1 to about 6.5 wt. %, about 1 to about 6 wt. %, about 1 to about 5 wt. %, about 1 to about 4 wt. %, about 1 to about 3 wt. %; about 2 to about 10 wt. %, about 2 to about 9 wt. %, about 2 to about 8 wt. %, about 2 to about 7 wt. %, about 2 to about 6.5 wt. %, about 2 to about 6 wt. %, about 2 to about 5 wt. %; about 3 to about 10 wt. %, about 3 to about 9 wt. %, about 3 to about 8 wt. %, about 3 to about 7 wt. %, about 3 to about 6.5 wt. %, about 3 to about 6 wt. %, about 3 to about 5 wt. %; about 4 to about 10 wt. %, about 4 to about 9 wt. %, about 4 to about 8 wt. % about 4 to about 7 wt. %, about 4 to about 6.5 wt. %, about 4 to about 6 wt. %, or about 4 to about 5 wt. %, including ranges and sub-ranges therebetween, based on the total weight of the hair treatment composition.

Preferably, the hair treatment composition may include about 0.5 to about 4.5 wt. % of bis-cetearyl amodimethicone. In some cases, the silicone further includes dimethicone, amodimethicone, or a mixture thereof.

The term "amino-functionalized silicone" or "amino silicones" means a silicone containing at least one primary amino, secondary amino, tertiary amino and/or quaternary ammonium group. The structure of the amino-functionalized silicone may be linear or branched, cyclic or non-cyclic. The amino functional group may be at any position in the silicone molecule, preferably at the end of the backbone (for example, in the case of amodimethicones) and/or in the side chain.

Non-limiting examples of silicones include amine-functionalized silicones (e.g., amodimethicone), dimethicone, bis-aminopropyl dimethicone, trimethyl silylamodimethicone, dimethicone copolyols, etc. The hair treatment composition may include, in some instances, one or more silicones chosen from polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), bis-aminopropyl dimethicone, trimethylsilylamodimethicone, dimethicone copolyols, dimethicone copolyol esters, dimethicone copolyol quaternium nitrogen containing compounds, dimethicone copolyol phosphate esters, and mixtures thereof. For example, the one or more silicones may be or include one or more dimethicone copolyols. The copolyols may be chosen from Dimethicone PEG-8 Adipate, Dimethicone PEG-8 Benzoate, Dimethicone PEG-7 Phosphate, Dimethicone PEG-10 Phosphate, Dimethicone PEG/PPG-20/23 Benzoate, Dimethicone PEG/PPG-7/4 Phosphate, Dimethicone PEG/PPG-12/4 Phosphate, PEG-3 Dimethicone, PEG-7 Dimethicone, PEG-8 Dimethicone, PEG-9 Dimethicone, PEG-10 Dimethicone, PEG-12 Dimethicone, PEG-14 Dimethicone, PEG-17 Dimethicone, PEG/PPG-3/10 Dimethicone, PEG/PPG-4/12 Dimethicone, PEG/PPG-6/11 Dimethicone, PEG/PPG-8/14 Dimethicone, PEG/PPG-14/4 Dimethicone, PEG/PPG-15/15 Dimethicone, PEG/PPG-16/2 Dimethicone, PEG/PPG-17/18 Dimethicone, PEG/PPG-18/18 Dimethicone, PEG/PPG-19/19 Dimethicone, PEG/PPG-20/6 Dimethicone, PEG/PPG-20/15 Dimethicone, PEG/PPG-20/20 Dimethicone, PEG/PPG-20/23 Dimethicone, PEG/PPG-20/29 Dimethicone, PEG/PPG-22/23 Dimethicone, PEG/PPG-22/24 Dimethicone, PEG/PPG-23/6 Dimethicone, PEG/PPG-25/25 Dimethicone, PEG/PPG-27/27 Dimethicone, and a mixture thereof.

The silicone(s) may, optionally, include or be chosen from a siloxane with a methacrylic group on one of its molecular ends, polydimethylsiloxane containing a styryl group on one of its molecular ends, or a similar silicone compound containing unsaturated groups; butadiene; vinyl chloride; vinylidene chloride; methacrylonitrile; dibutyl fumarate; anhydrous maleic acid; anhydrous succinic acid; methacryl glycidyl ether; an organic salt of an amine, an ammonium salt, and an alkali metal salt of methacrylic acid, of itaconic acid, of crotonic acid, of maleic acid or of fumaric acid; a radical-polymerizable unsaturated monomer containing a sulfonic acid group such as a styrenesulfonic acid group; a quaternary ammonium salt derived from methacrylic acid, such as 2-hydroxy-3-methacryloxypropyltrimethylammonium chloride; and a methacrylic acid ester of an alcohol containing a tertiary amine group, such as a methacrylic acid ester of diethylamine.

In some cases, the silicones, optionally, include or are chosen from siloxanes having an organo functional group, such as polyalkylsiloxanes, where at least one alkyl radical is different than methyl, for example organopolysiloxanes having the INCI name Stearyl Dimethicone, Cetyl Dimethicone or C26-28 Alkyl Dimethicone, or, for example, polyarylsiloxanes and polyarylalkylsiloxanes, for example organopolysiloxanes having the INCI name Phenyl Trimethicone, Trimethylsiloxyphenyl Dimethicone or Dimethylphenyl Dimethicone, or, for example, organopolysiloxanes having an organofunctional radical such as an aminopropyl, aminopropyl-aminoethyl, aminopropyl-aminoisobutyl radical, for example organopolysiloxanes having the INCI name Amodimethicone, or, for example, organopolysiloxanes having a polyethylene glycol or polyalkylene glycol radical, for example organopolysiloxanes having the INCI name PEG-12 Dimethicone, PEG/PPG-25,25-Dimethicone or Cetyl PEG/PPG-15/15 Butyl Ether Dimethicone.

In some instances, an amino-functionalized silicones is selected from compounds having the following formula:

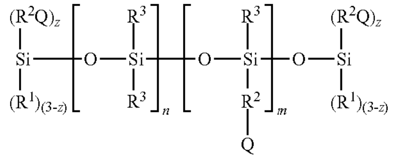

wherein each $R^1$ is independently selected from a $C_{1-30}$ alkyl group, a $C_{1-30}$ alkoxy group, a $C_{5-30}$ aryl group, a $C_{6-30}$ aralkyl group, a $C_{6-30}$ aralkyloxy group, a $C_{1-30}$ alkaryl group, a $C_{1-30}$ alkoxyaryl group, and a hydroxy group (preferably, each $R^1$ is independently selected from a $C_{1-30}$ alkyl group, a $C_{1-30}$ alkoxy group and a hydroxy group);

each $R^2$ is independently a divalent alkylene radical having one to ten carbon atoms (preferably, $R^2$ is a divalent alkylene radical having three to six carbon atoms);

each $R^3$ is independently selected from a $C_{1-30}$ alkyl group, a $C_{5-30}$ aryl group, a $C_{6-30}$ aralkyl group and a $C_{1-30}$ alkaryl group (preferably, each $R^3$ is independently selected from of a $C_{1-30}$ alkyl group);

Q is a monovalent radical selected from $—NR_2^4$ and $—NR^4(CH_2)_xNR_2^4$;

each $R^4$ is independently selected from a hydrogen and a $C_{1-4}$ alkyl group;

x is 2 to 6;

z is 0 or 1;

n is 25 to 3,000 (preferably, 25 to 2,000; more preferably, 25 to 1,000; most preferably 25 to 500); and m is 0 to 3,000 (preferably, 0 to 2,000; more preferably, 0 to 1,000; most preferably, 0 to 100);

with the proviso that at least 50 mol % of the total number of $R^1$ and $R^3$ groups are methyl and with the proviso that when mis 0, z is 1.

Preferred $R_1$ groups include methyl, methoxy, ethyl, ethoxy, propyl, propoxy, isopropyl, isopropoxy, butyl, butoxy, isobutyl, isobutoxy, phenyl, xenyl, benzyl, phenylethyl, tolyl and hydoxy. Preferred $R_2$ divalent alkylene radicals include trimethylene, tetramethylene, pentamethylene, $—CH_2CH(CH_3)CH_2—$ and $—CH_2CH_2CH(CH_3)CH_2—$. Preferred $R^3$ groups include methyl, ethyl, propyl, isopropyl, butyl, isobutyl, phenyl, xenyl, benzyl, phenylethyl and tolyl. Preferred $R^4$ groups include methyl, ethyl, propyl, isopropyl, butyl and isobutyl. When z is 0, the amino-functionalized silicine has only pendant amine functional substituents in the polymer chain. When z is 1, the amino-functional silicone may have only terminal amine functional substituents (e.g., m=0) or may have both terminal and pendant amine functional substituents in the polymer chain (e.g., m>0). Preferably, n+m is 50 to 1,000. More preferably, n+m is 50 to 750. Still more preferably, n+m is 50 to 500. Most preferably, n+m is 50 to 250.

In some instances, the amino-functionalized silicones are alkoxylated and/or hydroxylated amino silicones. Suitable alkoxylated and/or hydroxylated amino silicones may be selected from compounds of the following formula:

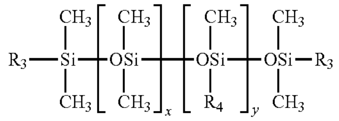

wherein $R_3$ is hydroxyl or $OR_5$, $R_5$ is a $C_1$ to $C_4$ alkyl group, $R_4$ is a group with structure according to the following formula:

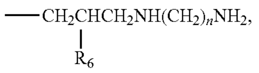

$R_6$ is a $C_1$ to $C_4$ alkyl, n is a 1 to 4, x is the same as "n" described above, and y is the same as "m" described above.

The silicone may be a polysiloxane corresponding to the following formula:

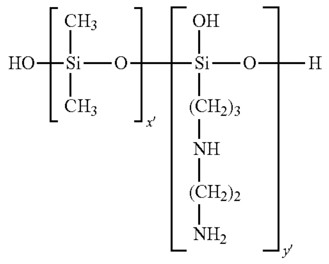

in which x' and y' are integers such that the weight-average molecular weight (Mw) is comprised between about 5000 and 500 000;

b) amino silicones corresponding to following formula:

$$R'_aG_{3-a}\text{-Si}(OSiG_2)_n\text{—}(OSiG_bR'_{2-b})_m\text{—O-Si}G_{3-a}\text{-}R'_a$$

in which:

G, which may be identical or different, designate a hydrogen atom, or a phenyl, OH or $C_1$-$C_8$alkyl group, for example methyl, or $C_1$-$C_8$ alkoxy, for example methoxy, a, which may be identical or different, denote the number 0 or an integer from 1 to 3, in particular 0;

b denotes 0 or 1, and in particular 1;

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

R', which may be identical or different, denote a monovalent radical having formula $-CqH_2qL$ in which q is a number ranging from 2 to 8 and L is an optionally quaternized amino group chosen from the following groups:

—NR"-Q-N(R")$_2$

—N(R")$_2$

—N+(R")$_3$A—

—N+H(R")$_2$A—

—N+H$_2$(R")A—

—N(R")—Q-N+R"H$_2$A—

—NR"-Q-N+(R")$_2$H A—

—NR"-Q-N+(R")$_3$A—, in which R", which may be identical or different, denote hydrogen, phenyl, benzyl, or a saturated monovalent hydrocarbon-based radical, for example a $C_1$-$C_{20}$ alkyl radical; Q denotes a linear or branched $CrH_{2r}$ group, r being an integer ranging from 2 to 6, preferably from 2 to 4; and A-represents a cosmetically acceptable ion, in particular a halide such as fluoride, chloride, bromide or iodide.

Another group of amino silicones corresponding to this definition is represented by silicones having the following formula:

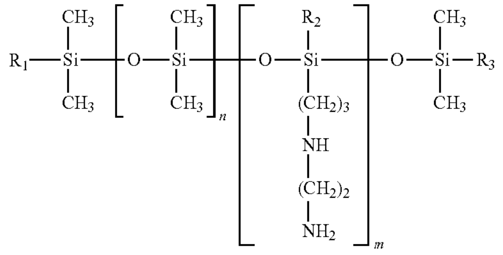

in which:

m and n are numbers such that the sum (n+m) can range from 1 to 1000, in particular from 50 to 250 and more particularly from 100 to 200, it being possible for n to denote a number from 0 to 999 and in particular from 49 to 249, and more particularly from 125 to 175, and for m to denote a number from 1 to 1000 and in particular from 1 to 10, and more particularly from 1 to 5;

$R_1$, $R_2$, $R_3$, which may be identical or different, represent a hydroxy or $C_1$-$C_4$ alkoxy radical, where at least one of the radicals $R_1$ to $R_3$ denotes an alkoxy radical.

The alkoxy radical is preferably a methoxy radical. The hydroxy/alkoxy mole ratio ranges preferably from 0.2:1 to 0.4:1 and preferably from 0.25:1 to 0.35:1 and more particularly equals 0.3:1. The weight-average molecular weight (Mw) of the silicone ranges preferably from 2,000 to 1,000,000, more particularly from 3,500 to 200,000.

Another group of amino silicones corresponding to this definition is represented by the following formula:

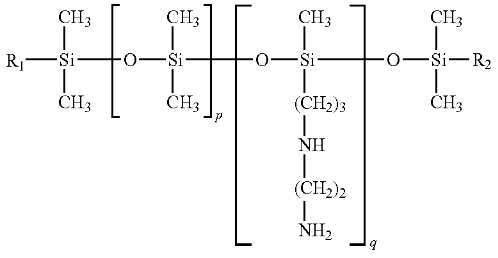

in which:

p and q are numbers such that the sum (p+q) ranges from 1 to 1000, particularly from 50 to 350, and more particularly from 150 to 250; it being possible for p to denote a number from 0 to 999 and in particular from 49 to 349, and more particularly from 159 to 239 and for q to denote a number from 1 to 1000, in particular from 1 to 10, and more particularly from 1 to 5;

$R_1$, $R_2$, which may be the same or different, represent a hydroxy or $C_1$-$C_4$ alkoxy radical, where at least one of the radicals $R_1$ or $R_2$ denotes an alkoxy radical.

The alkoxy radical is preferably a methoxy radical. The hydroxy/alkoxy mole ratio ranges generally from 1:0.8 to 1:1.1 and preferably from 1:0.9 to 1:1 and more particularly equals 1:0.95.

Another group of amino silicones is represented by the following formula:

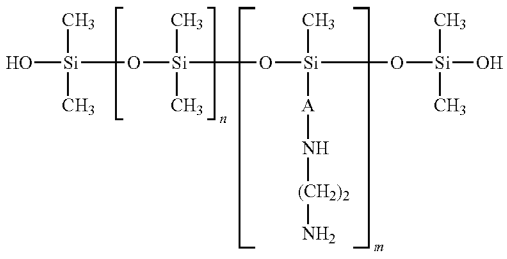

in which:

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

A denotes a linear or branched alkylene radical containing from 4 to 8 carbon atoms and preferably 4 carbon atoms. This radical is preferably linear.

The weight-average molecular weight (Mw) of these amino silicones ranges preferably from 2000 to 1 000 000 and even more particularly from 3500 to 200 000.

Another group of amino silicones is represented by the following formula:

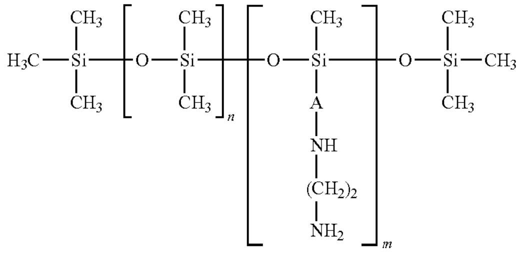

in which:

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

A denotes a linear or branched alkylene radical containing from 4 to 8 carbon atoms and preferably 4 carbon atoms. This radical is preferably branched.

The weight-average molecular weight (Mw) of these amino silicones ranges preferably from 500 to 1 000 000 and even more particularly from 1000 to 200 000.

Another group of amino silicones is represented by the following formula:

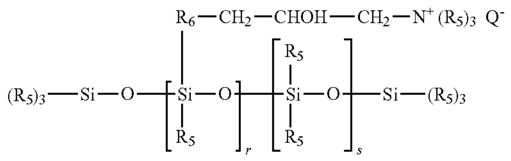

in which:

$R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

Q—is an anion such as a halide ion, in particular chloride, or an organic acid salt (for example acetate);

r represents a mean statistical value from 2 to 20 and in particular from 2 to 8;

s represents a mean statistical value from 20 to 200 and in particular from 20 to 50.

Such amino silicones are described more particularly in patent U.S. Pat. No. 4,185,087.

A group of quaternary ammonium silicones is represented by the following formula:

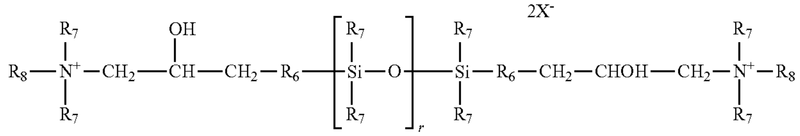

in which:

$R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring containing 5 or 6 carbon atoms, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

$R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a —$R_6$—$NHCOR_7$ radical;

X− is an anion such as a halide ion, in particular chloride, or an organic acid salt (for example acetate);

r represents a mean statistical value from 2 to 200 and in particular from 5 to 100. These silicones are described, for example, in patent application EP-A 0530974.

A group of quaternary ammonium silicones is represented by the following formula:

(J)

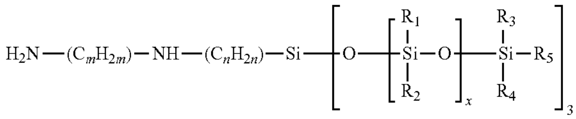

in which:

$R_1$, $R_2$, $R_3$ and $R_4$, which may be identical or different, denote a $C_1$-$C_4$ alkyl radical or a phenyl group;

$R_5$ denotes a $C_1$-$C_4$ alkyl radical or a hydroxyl group;

n is an integer ranging from 1 to 5;

m is an integer ranging from 1 to 5;

and in which x is chosen such that the amine number is between 0.01 and 1 meq/g;

multiblockpolyoxyalkylenated amino silicones, of type (AB)n, A being a polysiloxane block and B being a polyoxyalkylenated block containing at least one amine group.

Said silicones are preferably constituted of repeating units having the following general formulae:

$$[\text{—}(SiMe_2O)xSiMe_2\text{—}R\text{—}N(R'')\text{—}R'\text{—}O(C_2H_4O)_a(C_3H_6O)b\text{-}R'\text{—}N(H)\text{—}R\text{—}]$$

or alternatively $$[\text{—}(SiMe_2O)xSiMe_2\text{—}R\text{—}N(R'')\text{—}R'\text{—}O(C_2H_4O)_a(C_3H_6O)b\text{-}]$$

in which:

a is an integer greater than or equal to 1, preferably ranging from 5 to 200, more particularly ranging from 10 to 100;

b is an integer comprised between 0 and 200, preferably ranging from 4 to 100, more particularly between from 5 and 30;

x is an integer ranging from 1 to 10 000, more particularly from 10 to 5000;

R'' is a hydrogen atom or a methyl;

R, which may be identical or different, represent a divalent linear or branched $C_2$-$C_{12}$ hydrocarbon-based radical, optionally including one or more heteroatoms such as oxygen; preferably, R denotes an ethylene radical, a linear or branched propylene radical, a linear or branched butylene radical, or a —$CH_2CH_2CH_2OCH(OH)CH_2$— radical; preferentially R denotes a —$CH_2CH_2CH_2OCH(OH)CH_2$— radical;

R', which may be identical or different, represent a divalent linear or branched $C_2$-$C_{12}$ hydrocarbon-based radical, optionally including one or more heteroatoms such as oxygen; preferably, R' denotes an ethylene radical, a linear or branched propylene radical, a linear or branched butylene radical, or a —$CH_2CH_2CH_2OCH(OH)CH_2$— radical; preferentially R' denotes —$CH(CH_3)$—$CH_2$—.

The siloxane blocks preferably represent between 50 and 95 mol % of the total weight of the silicone, more particularly from 70 to 85 mol %.

The amine content is preferably between 0.02 and 0.5 meq/g of copolymer in a 30% solution in dipropylene glycol, more particularly between 0.05 and 0.2. The weight-average molecular weight (Mw) of the silicone oil is preferably comprised between 5000 and 1,000,000, more particularly between 10,000 and 200,000.

The silicone may be selected from those having at least one quaternary ammonium group. Suitable non-limiting examples are quaternium 80, silicone quaternium-1, silicone quaternium-2, silicone quaternium-2 panthenol succinate, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-16/Glycidoxy Dimethicone Crosspolymer, silicone quaternium-17, silicone quaternium-18, silicone quaternium-20 and silicone quaternium-21. Preferred are quaternium 80, silicone quaternium-16, silicone quaternium-18, silicone quaternium-1, silicone quaternium-2, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-17, silicone quaternium-20 and silicone quaternium-21. More preferred are quaternium 80, silicone quaternium-16, silicone quaternium-18, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, and silicone quaternium-17. Preferred are quaternium 80, silicone quaternium-16, silicone quaternium-18, silicone quaternium-15, and mixtures thereof. In an embodiment, the one or more silicone oils of the present disclosure is a non-amino silicone oil such as a dimethicone.

Non-limiting examples of amino-functionalized silicones include bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof. In some instances, a particularly useful amino-functionalized silicone is bis-hydroxy/methoxy amodimethicone, wherein X is isobutyl and one of the R is OH and the other is $OCH_3$ in the above structure, also known as "Bis-Hydroxy/Methoxy Amodimethicone" and "3-[(2-aminoethyl)amino]-2-methylpropyl Me, di-Me, [(hydroxydimethylsilyl)oxy]- and [(methoxydimethylsilyl)oxy]-terminated." Bis-hydroxy/methoxy amodimethicone is commercially available under the tradename DOWSIL AP-8087 FLUID from The Dow Chemical Company. A non-limiting example of amodimethicone products containing amino silicones having structure (D) re sold by Wacker under the name BELSIL ADM 652, BELSIL ADM 4000 E, or BELSIL ADM LOG 1. A product containing amino silicones having structure (E) is sold by Wacker under the name FLUID WR 1300. Additionally or alternative, the weight-average molecular weight (Mw) of the silicone ranges preferably from 2,000 to 200,000, even more particularly 5,000 to 100,000 and more particularly from 10,000 to 50,000.

The silicone(s) in the hair treatment compositions of the instant disclosure are included in the form of a silicone emulsion comprising at least one silicone and at least one surfactants, for example, nonionic surfactants, cationic surfactants, amphoteric surfactants, anionic surfactants. The silicone emulsions can be nanoemulsions, microemulsions or macroemulsions. Suitable examples of nonionic surfactants are alkoxylated fatty alcohols or polyethylene glycol ethers of mixtures of C8-C30 fatty alcohols with an average of number of moles of ethylene oxide such as C11-15 Pareth-7, laureth-9, laureth-12, deceth-7, deceth-10, trideceth-6, trideceth-10, trideceth-12, or a mixture thereof. Suitable examples of amphoteric surfactants are cocamidopropyl betaine, coco-betaine, or a mixture thereof. Suitable examples of cationic surfactants are quaternary ammonium compounds such as behentrimonium chloride, cetrimoinium chloride, behentrimonium methosulfate, or a mixture thereof. Suitable examples of anionic surfactants are sulfate-based compounds such as further comprises up to 5 wt. % of a surfactant, for example, sodium (or ammonium) lauryl sulfate, sodium (or ammonium) laureth sulfate, or mixtures thereof.

Water

The hair treatment composition includes water. The amount of water in the hair treatment may vary, but typically ranges from about 40 to about 78 wt. %, about 45 to about 78 wt. %, about 50 to about 78 wt. %, about 55 to about 78 wt. %, about 60 to about 78 wt. %, about 62.5 to about 78 wt. %, about 65 to about 78 wt. %, about 70 to about 78 wt. %; about 40 to about 70 wt. %, about 45 to about 70 wt. %, about 50 to about 70 wt. %, about 55 to about 70 wt. %, about 62.5 to about 70 wt. %, about 60 to about 70 wt. %, about 65 to about 70 wt. %; about 40 to about 67 wt. %, about 45 to about 67 wt. %, about 50 to about 67 wt. %, about 55 to about 67 wt. %, about 60 to about 67 wt. %, or about 62.5 to about 67 wt. %, including all ranges and sub-ranges therebetween, based on the total weight of the hair treatment composition.

Polyol(s)

The hair treatment compositions may optionally include one or more polyols. The amount of polyol(s) present in the hair treatment composition typically ranges from about 1 to about 10 wt. %, based on the total weight of the hair treatment composition. For example, the amount of polyol(s) in the hair treatment composition may be about 1 to about 10 wt. %, about 2 to about 10 wt. %, about 3 to about 10 wt. %, about 4 to about 10 wt. %, about 5 to about 10 wt. %, about 6 to about 10 wt. %, about 7 to about 10 wt. %; about 1 to about 8 wt. %, about 2 to about 8 wt. %, about 3 to about 8 wt. %, about 4 to about 8 wt. %, about 5 to about 8 wt. %, about 6 to about 8 wt. %; about 1 to about 6 wt. %, about 2 to about 6 wt. %, about 3 to about 6 wt. %, about 4 to about 6 wt. %, or about 5 to about 6 wt. %, including all ranges and sub-ranges therebetween, based on the total weight of the hair treatment composition.

The term "polyol" should be understood as meaning, within the meaning of the present disclosure, an organic molecule comprising at least two free hydroxyl groups. The polyols of the hair treatment composition may be glycols or compounds with numerous hydroxyl groups. In some cases, the one or more polyols is/are selected from the group consisting of C2-C32 polyols. The one or more polyols may be liquid at ambient temperature (25° C.). The one or more polyols may have from 2 to 32 carbon atoms, from 3 to 16 carbon atoms, or from 3 to 12 carbon atoms.

Polyols that may be included in the hair treatment composition, in certain instances, include ethylene glycol, propylene glycol, butylene glycol, hexylene glycol, glycerin, diglycerin, diethylene glycol, and dipropylene glycol, and mixtures thereof. In some cases, the polyol is propylene glycol. In some further cases, the polyol is one or both of propylene glycol and butylene glycol. Additionally, in some cases, the hair treatment composition comprises at least propylene glycol, and optionally one or more polyols other than propylene glycol.

Non-limiting examples of polyols that may, optionally, be included in the hair treatment include and/or may be chosen from alkanediols such as glycerin, 1,2,6-hexanetriol, trimethylolpropane, ethylene glycol, propylene glycol, butylene glycol, pentylene glycol, hexylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, dipropylene glycol mono-iso-propyl ether, sorbitol, sorbitan, triacetin, and a mixture thereof.

The one or more polyols may, optionally, be glycols or glycol ethers such as, e.g., monomethyl, monoethyl and monobutyl ethers of ethylene glycol, propylene glycol or ethers thereof such as, e.g., monomethyl ether of propylene glycol, butylene glycol, hexylene glycol, dipropylene glycol as well as alkyl ethers of diethylene glycol, e.g., monoethyl ether or monobutyl ether of diethylene glycol. In some cases, the one or more polyols may include or are chosen from ethylene glycol, propylene glycol, butylene glycol, hexylene glycol, pentylene glycol, 1,3-propanediol, diethylene glycol, dipropylene glycol, 1,4-butanediol, 1,5-pentanediol, hexane-1,6-diol, glycerin, diglycerin, caprylyl glycol, and a mixture thereof.

Kits

Aspects of the instant disclosure are directed to kits, which include the hair treatment compositions discussed herein. The kits typically include at least one hair treatment composition according to the instant disclosure and one or more additional compositions, such as a shampoo, a mask, serum, etc. The various compositions are separately contained in the kits. For example, the kits may include one or more hair treatment compositions, a shampoo, a mask, and/or other hair treatment products, all of which are separately contained.

The hair treatment compositions disclosed herein may provide especially improved results with certain shampoo compositions. For example, the hair treatment composition may provide better results when used in conjunction (simultaneously or consecutively) with certain shampoos. In some instances, the shampoo composition may be formulated to effect the hair, such that the hair treatment composition provides more beneficial properties to the hair.

The shampoo compositions may be sulfate-based, contain non-sulfate surfactants, be sulfate free, and/or be free of anionic surfactants. In some cases the shampoo composition includes about 0.3 to 35 wt. % of a nonionic surfactant; optionally, about 1 to about 30 wt. % of an anionic surfactant; about 0.1 to about 50 wt. % of a polyol; about 0.1 to about 5 wt. % of a silicone; and water, wherein all weight percentages are based on the total weight of the shampoo. The shampoos may contain surfactants including, but not limited to, alkyl polyglucosides such as decyl glucoside, coco-glucoside, lauryl glucoside; amionic surfactants such as sodium lauryl sulfate, sodium laureth sulfate, sodoium lauryl methyl isethionate, sodium cocoyl isethionate, disodium laureth sulfosuccinate (and) sodium lauryl sulfoacetate; amphoteric surfactants such ascocamidopropyl betaine and coco-betaine; nonionic surfactants such as alkoylated fatty alcohols, for exampleppg-5-ceteth-20, laureth-12, etc., cocamide mea, and cocodiamphoacetate salts.

In at least one embodiment, the shampoo composition has a formulation according to the following table.

TABLE 1

| US INCI Name | Wt. % |
|---|---|
| COCO-BETAINE | 1 to 15 |
| SODIUM LAUROYL SARCOSINATE | 2 to 20 |
| DECYL GLUCOSIDE | 1 to 15 |
| SODIUM COCOYL ISETHIONATE | 2 to 15 |
| COCAMIDOPROPYL BETAINE | 1 to 15 |
| DISODIUM LAURETH SULFOSUCCINATE (and) SODIUM LAURYL SULFOACETATE | 5-25 |
| PPG-5-CETETH-20 | <5 |
| CARBOMER | <5 |
| AQUA | QS 100 |
| GLYCOL DISTEARATE | 1 to 2 |

TABLE 1-continued

| US INCI Name | Wt. % |
|---|---|
| PRESERVATIVES | <3 |
| POLYQUATERNIUM-10 | <15 |
| AMODIMETHICONE | 0.1 to 5 |

In at least one other embodiment, the shampoo composition has a formulation according to the following table.

TABLE 2

| US INCI Name | Wt. % |
|---|---|
| COCO-BETAINE | 10 to 15 |
| LAURETH-12 | <1 |
| COCAMIDE MEA | <5 |
| SODIUM LAURETH SULFATE | 10 to 20 |
| SODIUM CHLORIDE | 1 to 3 |
| HEXYLENE GLYCOL | 0.1 to 5 |
| SODIUM BENZOATE | <1 |
| GLYCERIN | 1 to 3 |
| FRAGRANCE | <1 |
| WATER | QS 100 |

The hair treatment compositions and/or shampoos of the kit may be packaged in a variety of different containers, such as, for example, a ready-to-use container. Non-limiting examples of useful packaging include tubes, jars, caps, unit dose packages, and bottles, including squeezable tubes, bottles, and sprayable containers. The packaging may be configured so that it can be attached to a wall, such as a wall in a bathroom, including walls of a shower or tub. For example, the packaging can be a container that is configured to attach to a wall, such that when pressure is applied to the container, the composition contained therein is expelled from one or more openings in the container. In some cases, the packaging is a tube, such as a tube with two compartments, or dual tubes, each forming a separate compartment. Each compartment may include a different composition. For example, one tube or compartment may include a hair treatment composition according to the instant disclosure, and the other tube may include a composition to be used with the hair treatment composition, for example, a shampoo, a conditioner, an all-in-one shampoo/conditioner (i.e., a conditioning shampoo; also referred to as a "co-wash") mask or other hair treatment products.

Method of Making

The hair treatment compositions may be produced using typical equipment used to produce hair treatment compositions, such as conditioners. For example, the hair treatment composition may be produced using one or more of the following steps: combining a portion of the water with the thickening agent (e.g., a natural cellulose or gum); mixing the foregoing combination at a temperature of over 60° C.; adding ingredients that melt/dissolve at the heated temperature and/or that do not evaporate at the heated temperature; optionally, mixing and/or using shear to emulsify the ingredients; cooling the combination of ingredients; adding ingredients to the cooled down combination that would evaporate and/or degrade at the heated temperature; add a remainder of water; mixing until the hair treatment compositions is uniform. One of ordinary skill in the art would readily understand how to make the hair treatment compositions based on the disclosure herein.

Method(s) for Treating Hair

Aspects of the instant disclosure also relate to methods for the hair treatment compositions disclosed herein. A method for treating hair according to aspects of the disclosure typically includes:

(I) optionally, applying a shampoo to hair;

(II) optionally, rinsing the hair to remove at least a portion of the shampoo;

(III) applying a hair treatment composition comprising:

(a) about 2 to about 6 wt. % of two or more cationic surfactants comprising a di-alkyl dimonium halide compound or salt thereof and a mono-alkyl trimonium halide compound or salt thereof, wherein a weight ratio of the total amount of di-alkyl dimonium halide compound or salt thereof to the total amount of mono-alkyl trimonium halide compound or salt thereof is about 1:10 to about 5:1;

(b) about 0.1 to about 10 wt. % of a thickening agent;

(c) about 10 wt. % or more of a fatty compound;

(d) about 0.1 to about 10 wt. % of a silicone; and (e) water, wherein all weight percentages are based on the total weight of the hair treatment composition; and (IV) optionally, rinsing the hair to remove at least a portion of the hair treatment composition.

The methods for treating and/or cleaning hair according to the disclosure may vary but typically include applying a hair treatment composition as disclosed herein, allowing the hair treatment composition to remain on the hair for a sufficient amount of time, and rinsing the hair treatment compositions from the hair. In some instances, however, the hair treatment composition may be a leave-in composition. For example, the hair treatment compositions may allowed to remain on the hair indefinitely, i.e., the hair treatment composition is not removed or rinsed from the hair prior to styling the hair.

The hair treatment composition according to the disclosure may be in the form of a thick or light cream, emulsion, or lotion.

The hair treatment composition according to the disclosure may be a hair conditioner product (rinse-off or leave-in), a mask product (rinse-off or leave-in), or a deep treatment product (rinse-off or leave-in).

The hair treatment composition may be applied to the hair in a sequence with other compositions. For example, the hair treatment composition may be applied to the hair before shampooing the hair, after shampooing the hair, before conditioning the hair, and/or after conditioning the hair, etc. The hair treatment compositions, however, are not required to be used in a sequence.

The methods may include applying an amount of the hair treatment composition onto the body, for example, onto one or both hands, onto the hair, onto the face, etc. The body may already be wet or damp with extraneous water or extraneous water can be included after the hair treatment composition has already been applied to the body. Alternatively, the hair treatment composition and extraneous water may be combined, and optionally mixed, prior to application to the body. For example, the hair treatment composition may be combined in a container, bowl, packaging, bottle, etc., and subsequently applied to the hair.

In some cases, the hair treatment compositions are used in conjunction with additional hair-care compositions in a routine, for example, during an individual's normal showering/bathing routine. The hair treatment composition may be applied to the hair individually or may be combined with one or more additional compositions. For instance, the hair treatment composition may be mixed with a shampoo (or conditioner) prior to application to the hair. In this case, the mixture of the shampoo (or conditioner) and the hair treatment composition are simultaneously applied to the hair during the cleansing or conditioning process and simultaneously rinsed from the hair. Alternatively, the hair treatment composition may be layered on top of (or lathered into) hair to which a shampoo (or conditioner) has already been applied or vice versa. In this case, the hair treatment composition may be applied to the hair and without rinsing it from the hair, a shampoo (or conditioner) is then subsequently applied to the hair. Alternatively, the shampoo (or conditioner) may be first applied to the hair and without rinsing the shampoo (or conditioner) from the hair, the hair treatment composition is also applied to the hair.

When used in conjunction with a shampoo and/or a conditioner, the hair treatment composition may be mixed or used with the shampoo and/or conditioner in a ratio of about 1:10 to about 10:1, about 1:5 to about 5:1, about 1:3 to about 3:1, about 1:2 to about 2:1, about 1:1 to about 4:1, about 1:1 to about 3:1, or about 1:1 to about 2:1 (hair treatment composition of the instant disclosure: shampoo/conditioner, etc.).

The hair treatment compositions of the instant disclosure may be allowed to remain on the hair for a minimum amount of time before being rinsed from the hair, but it is not necessary to allow the hair treatment composition to remain on the hair for an extended period of time. Conveniently, the hair treatment compositions can be applied and allowed to remain on the hair for a period of time that is typical for regular shampooing and/or conditioning. For example, the hair treatment composition (whether combined with another hair-treatment composition such as a shampoo or conditioner) may be applied to the hair and allowed to remain on the hair for a few seconds (1, 2, 3, or 5 seconds) up to about 1, about 2, about 5, about 10, about 15, about 20, about 25, or about 30 minutes.

When the hair treatment composition is not being mixed with another composition prior to application to the hair, the hair treatment composition may be applied to the hair immediately after or before the hair is treated with another composition (e.g., a shampoo and/or a conditioner). For example, the hair treatment compositions may be applied to the hair within about a few seconds or 1, 2, 5, 10, or 20 minutes before or after a shampoo and/or a conditioner is applied to the hair.

The term "INCI" is an abbreviation of International Nomenclature of Cosmetic Ingredients, which is a system of names provided by the International Nomenclature Committee of the Personal Care Products Council to describe personal care ingredients.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

All components and elements positively set forth in this disclosure can be negatively excluded from the claims. In other words, the hair cleansing compositions of the instant disclosure can be free or essentially free of all components and elements positively recited throughout the instant disclosure. In some instances, the hair cleansing compositions of the present disclosure may be substantially free of non-incidental amounts of the ingredient(s) or compound(s) described herein. A non-incidental amount of an ingredient or compound is the amount of that ingredient or compound that is added into the hair cleansing composition by itself. For example, a hair cleansing composition may be substantially free of a non-incidental amount of an ingredient or compound, although such ingredient(s) or compound(s) may be present as part of a raw material that is included as a blend of two or more compounds.

Some of the various categories of components identified may overlap. In such cases where overlap may exist and the hair cleansing composition includes both components (or the composition includes more than two components that overlap), an overlapping compound does not represent more than one component. For example, certain compounds may be characterized as both an emulsifier and a surfactant. If a particular hair composition includes both an emulsifier and a surfactant, the compounds that may be characterized as both an emulsifier and a surfactant will serve only as either the emulsifier or the surfactant—not both.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

As used herein, the terms "comprising," "having," and "including" are used in their open, non-limiting sense. The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

The expression "one or more" means "at least one" and thus includes individual components as well as mixtures/combinations. Other than in the operating examples, or where otherwise indicated, all numbers expressing quantities of ingredients and/or reaction conditions may be modified in all instances by the term "about," meaning within +/−5% of the indicated number.

The term "treat" (and its grammatical variations) as used herein refers to the application of the compositions of the present disclosure onto the surface of keratinous substrates such as hair on a user's head and/or body.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of silicones.

EMBODIMENTS OF THE DISCLOSURE

In accordance with a first embodiment, provided is a hair treatment composition including:

about 2 to about 6 wt. %, preferably about 2 to about 5 wt. %, more preferably about 3 to about 5 wt. % of two or more cationic surfactants comprising a di-alkyl dimonium halide compound or salt thereof and a mono-alkyl trimonium halide compound or salt thereof;

wherein a weight ratio of the total amount of di-alkyl dimonium halide compound or salt thereof to the total amount of mono-alkyl trimonium halide compound or salt thereof is about 1:10 to about 5:1, preferably about 1:8 to about 5:1, more preferably about 1:5 to about 1:1, about 0.1 to about 10 wt. %, preferably about 0.1 to about 8 wt. %, more preferably about 0.5 to about 7 wt. %, of a thickening agent chosen from xanthan gum, guar gum, biosaccharide gum, cellulose, acacia seneca gum, *sclerotium* gum, agarose, pechtin, gellan gum, hyaluronic acid, and a mixture thereof;

about 10 wt. % or more, preferably about 10 to about 40 wt. %, more preferably about 10 to about 20 wt. %, of a fatty compound chosen from a fatty alcohol, a fatty ester, a fatty acid, a wax, an oil, a derivative thereof, and a mixture thereof;

about 0.5 to about 10 wt. %, preferably about 0.5 to about 6.5 wt. %, more preferably about 1 to about 6.5 wt. %, of a silicone, such as bis-cetearyl amodimethicone, dimethicone, amodimethicone, or a mixture thereof; and water, preferably in an amount of about 40 to about 78 wt. %, preferably about 50 to about 78 wt. %, or more preferably about 50 to about 70 wt. %, wherein all weight percentages are based on the total weight of the hair treatment composition.

According to another embodiment, provided is a hair treatment composition including:

about 2 to about 6 wt. %, preferably about 2 to about 5 wt. %, more preferably about 3 to about 5 wt. % of two or more cationic surfactants comprising:

(i) about 0.5 to about 5 wt. %, preferably 0.5 to 2.5 wt. % of dicetyldimonium chloride, and (ii) about 0.5 to about 5.5 wt. %, preferably 2.5 to about 4.8 wt. % of behentrimonium chloride, wherein a weight ratio of the dicetyldimonium chloride to the behentrimonium chloride is about 1:10 to about 5:1, preferably about 1:8 to about 5:1, more preferably about 1:5 to about 1:1, about 0.1 to about 10 wt. %, preferably about 0.1 to about 8 wt. %, more preferably about 0.5 to about 7 wt. %, of a thickening agent chosen from xanthan gum, guar gum, biosaccharide gum, cellulose, acacia seneca gum, *sclerotium* gum, agarose, pechtin, gellan gum, hyaluronic acid, and a mixture thereof;

about 10 wt. % or more, preferably about 10 to about 40 wt. %, more preferably about 10 to about 20 wt. %, of a fatty compound chosen from a fatty alcohol, a fatty ester, a fatty acid, a wax, an oil, a derivative thereof, and a mixture thereof;

about 0.5 to about 6.5 wt. %, preferably about 1 to about 6.5 wt. %, more preferably 1 to about 5 wt. %, of bis-cetearyl amodimethicone;

water, preferably in an amount of about 40 to about 78 wt. %, preferably about 50 to about 78 wt. %, or more preferably about 50 to about 70 wt. %; and about 1 wt. % to about 10 wt. %, preferably about 2 to about 10 wt. %, more preferably about 3 to about 8 wt. %, of a polyol including, e.g., ethylene glycol, propylene glycol, butylene glycol, hexylene glycol, pentylene glycol, diethylene glycol, dipropylene glycol, caprylyl glycol, 1,3 propanediol, glycerin, diglycerin, polyethylene glycols, and a mixture thereof, wherein all weight percentages are based on the total weight of the hair treatment composition.

According to yet another embodiment, provided is a method for treating hair inducing:

(I) optionally, applying a shampoo to hair;

(II) optionally, rinsing the hair to remove at least a portion of the shampoo;

(III) applying a hair treatment composition comprising:

about 2 to about 6 wt. %, preferably about 2 to about 5 wt. %, more preferably about 3 to about 5 wt. % of two or more cationic surfactants comprising a di-alkyl dimonium halide compound or salt thereof and a mono-alkyl trimonium halide compound or salt thereof;

wherein a weight ratio of the total amount of the di-alkyl dimonium halide compound or salt thereof to the total amount of the mono-alkyl trimonium halide compound or salt thereof is about 1:10 to about 5:1, preferably about 1:8 to about 5:1, more preferably about 1:5 to about 1:1, about 0.1 to about 10 wt. %, preferably about 0.1 to about 8 wt. %, more preferably about 0.5 to about 7 wt. %, of a thickening agent chosen from xanthan gum, guar gum, biosaccharide gum, cellulose, acacia seneca gum, sclerotium gum, agarose, pechtin, gellan gum, hyaluronic acid, and a mixture thereof;

about 10 wt. % or more, preferably about 10 to about 40 wt. %, more preferably about 10 to about 20 wt. %, of a fatty compound chosen from a fatty alcohol, a fatty ester, a fatty acid, a wax, an oil, a derivative thereof, and a mixture thereof;

about 0.5 to about 10 wt. %, preferably about 0.5 to about 6.5 wt. %, more preferably about 1 to about 6.5 wt. %, of a silicone, such as bis-cetearyl amodimethicone, dimethicone, amodimethicone, or a mixture thereof; and water, preferably in an amount of about 40 to about 78 wt. %, preferably about 50 to about 78 wt. %, or more preferably about 50 to about 70 wt. %, wherein all weight percentages are based on the total weight of the hair treatment composition.

(IV) optionally, rinsing the hair to remove at least a portion of the hair treatment composition.

EXAMPLES

Implementation of the present disclosure is provided by way of the following examples. The following examples serve to elucidate aspects of the technology without being limiting in nature.

Example 1

Two exemplary hair treatment compositions (Exemplary Compositions A and B) were prepared in accordance with aspects of the disclosure.

TABLE 3

| | | INCI Name | Ex. A | Ex. B |
|---|---|---|---|---|
| (a) | Cationic Surfactant | CETRIMONIUM CHLORIDE | ~0.1 | ~0.1 |
| | | DICETYLDIMONIUM CHLORIDE | 1.1 | 1.1 |
| | | BEHENTRIMONIUM CHLORIDE | 3.6 | 3.6 |
| Weight ratio of the dicetyldimonium chloride to the behentrimonium chloride | | | 1:3.4 | 1:3.4 |
| (b) | Thickening Agent | HYDROXYPROPYL GUAR | 0.5 | 0.5 |
| (c) | Fatty Compounds | CETEARYL ALCOHOL | 12 | 12 |
| | | EUPHORBIA CERIFERA (CANDELILLA) WAX, ISOPROPYL MYRISTATE, and CETYL ESTERS | 2.5 | 2.5 |
| (d) | Silicone | DIMETHICONE | 3.4 | 3.4 |
| | | AMODIMETHICONE | 0.1 | 0.1 |
| | | BIS-CETEARYL AMODIMETHICONE* | 1.8 | 1.8 |
| (f) | Polyol | GLYCERIN | 5 | 5 |
| | Nonionic Surfactants | ONE OR MORE OF TRIDECETH-3, TRIDECETH-10, STEARETH-6, and/or PEG-100 STEARATE | <0.1 | <0.1 |
| | Amphoteric surfactant | COCO-BETAINE | <0.5 | |
| | Mono-alcohol | ISOPROPYL ALCOHOL | 1.1 | 1.1 |
| | Miscellaneous (One or more of Preservative(s), Chelating Agent(s), Antioxidant(s), Fragrance, pH Adjuster(s), and/or Salt(s)) | PHENOXYETHANOL, DILAURYL THIODIPROPIONATE, TRISODIUM HEDTA, ACETIC ACID, CITRIC ACID, SODIUM CITRATE, SODIUM CHLORIDE, ETHANOLAMINE, and/or FRAGRANCE | 3.4 | 4.3 |
| (e) | Water | WATER | QS to 100 | QS to 100 |

*Available under the tradename of SILSOFT AX, from Momentive Performance Materials

Example 2

An exemplary shampoo was prepared having the formulation shown in Table 4, provided below.

TABLE 4

| | INCI Name | Ex. Shampoo |
|---|---|---|
| onionic Surfactant | SODIUM COCOYL ISETHIONATE | 11 |
| | DECYL GLUCOSIDE | 11.7 |
| | COCAMIDOPROPYL BETAINE | 2.6 |
| | TRIDECETH-6 | 0.02 |
| | PEG-55 PROPYLENE GLYCOL OLEATE | 0.4 |
| | PPG-5-CETETH-20 | 0.2 |
| Amphoteric surfactant | COCO-BETAINE | 0.024 |
| Polyol(s) | GLYCERIN and PROPYLENE GLYCOL | 1.2 |
| Cationic Polymer | POLYQUATERNIUM-67 | 0.2 |
| Fatty Ester | COCO-CAPRYLATE/CAPRATE, GLYCOL DISTEARATE, and PEG-150 DISTEARATE | 0.8 |
| Silicone | DIMETHICONE and AMODIMETHICONE | 0.9 |
| Thickening Agents | ACRYLATES/BEHENETH-25 METHACRYLATE COPOLYMER and CARBOMER | 0.3 |
| Miscellaneous (One or more of Preservative(s), Chelating Agent(s), Antioxidant(s), Fragrance, pH Adjuster(s), and/or Salt(s)) | SALICYLIC ACID, PANTHENOL, CITRIC ACID, SODIUM BENZOATE, CETRIMONIUM CHLORIDE, FRAGRANCE, SODIUM CHLORIDE, and ETHANOLAMINE | 3.4 |
| Water | WATER | QS to 100 |

Example 3

The color preservation of Exemplary Composition A was evaluated in comparison to four comparative hair treatment compositions (Comparative Compositions 1-4). Comparative Compositions 1-4 were prepared to have formulations similar to Exemplary Composition A, except that each of Comparative Compositions 1-4 did not include one of hydroxypropyl guar, bis-cetearyl amodimethicone, dicetyldimonium chloride, and behentrimonium chloride. The formulations for Comparative Compositions 1-4 are shown in Table 5, below.

TABLE 5

| | | INCI Name | Comp. 1 | Comp. 2 | Comp. 3 | Comp. 4 |
|---|---|---|---|---|---|---|
| (a) | Cationic Surfactant | CETRIMONIUM CHLORIDE | ~0.1 | ~0.1 | ~0.1 | ~0.1 |
| | | DICETYLDIMONIUM CHLORIDE | 1.1 | | 1.1 | 1.1 |
| | | BEHENTRIMONIUM CHLORIDE | 3.6 | 3.6 | | 3.6 |
| weight ratio of the dicetyldimonium chloride to the behentrimonium chloride | | | 1:3.4 | 0:3.4 | 1:0 | 1:3.4 |
| (b) | Thickening Agent | HYDROXYPROPYL GUAR | 0.5 | 0.5 | 0.5 | |
| (c) | Fatty Compounds | CETEARYL ALCOHOL | 12 | 12 | 12 | 12 |
| | | EUPHORBIA CERIFERA (CANDELILLA) WAX, ISOPROPYL MYRISTATE, and CETYL ESTERS | 2.5 | 2.5 | 2.5 | 2.5 |
| (d) | Silicone | DIMETHICONE | 3.4 | 3.4 | 3.4 | 3.4 |
| | | AMODIMETHICONE | 0.1 | 0.1 | 0.1 | 0.1 |
| | | BIS-CETEARYL AMODIMETHICONE | | 1.8 | 1.8 | 1.8 |
| (f) | Polyol | GLYCERIN | 5 | 5 | 5 | 5 |
| | Nonionic Surfactants | ONE OR MORE OF TRIDECETH-3, TRIDECETH-10, STEARETH-6, and PEG-100 STEARATE | <0.1 | <0.1 | <0.1 | <0.1 |
| | Amphoteric surfactant | COCO-BETAINE | <0.5 | <0.5 | <0.5 | <0.5 |
| | Mono-alcohol | ISOPROPYL ALCOHOL | 1.1 | 1.1 | | 1.1 |
| | Miscellaneous (One or more of Preservative(s), Chelating Agent(s), Antioxidant(s), Fragrance, pH Adjuster(s), and/or Salt(s) | PHENOXYETHANOL, DILAURYL THIODIPROPIONATE, TRISODIUM HEDTA, ACETIC ACID, CITRIC ACID, SODIUM CITRATE, SODIUM CHLORIDE, ETHANOLAMINE, and/or FRAGRANCE | 3.4 | 3.4 | 3.4 | 3.4 |
| (e) | Water | WATER | QS to 100 | QS to 100 | QS to 100 | QS to 100 |

A highlighter composition was applied to six Caucasian virgin hair swatches. After giving the hair swatches color highlights, each hair swatch received the same amount of Exemplary Shampoo (discussed above), massaged, and then rinsed for about 2 minutes. Excess water was removed from each of the hair swatches. Exemplary Composition A and Comparative Compositions 1-4 were applied to respective hair swatches, left on the hair swatches for 1 minute, and then the hair swatches were rinsed. After rinsing, the hair swatches were dried with a blower. This procedure of washing the hair swatches by applying the Exemplary Shampoo, applying the respective hair treatment compositions, and then blow drying the hair swatches was completed for a total of 5 cycles. A control was prepared by following the foregoing procedure of washing the hair swatches by applying the Exemplary Shampoo, blow drying the hair swatch, and repeating this procedure for a total of 5 cycles.

The hair swatches were visually evaluated to determine the color preservation for each of Exemplary Composition A and Comparative Compositions 1-4, the results of which are presented in Table 6.

TABLE 6

| Main constituents | Ex. A | Comp. 1 | Comp. 2 | Comp. 3 | Comp. 4 |
|---|---|---|---|---|---|
| Hydroxypropyl Guar | • | • | • | • | |
| Bis-cetearyl Amodimethicone | • | | • | • | • |
| Dicetyldimonium Chloride | • | • | | • | • |
| Behentrimonium Chloride | • | • | • | | • |
| Attribute | | | | | |
| Tone preservation effect | +++ | = | ++ | + | + |

A "=" was given to compositions that exhibited color preservation equal to the control. A "+" was given to compositions that exhibited slightly better color preservation than the control. A "++" was given to compositions that exhibited superior color preservation than the control. A "+++" was given to compositions that exhibited a significantly superior color preservation than the control.

As seen in Table 6, Exemplary Composition A exhibited a significantly superior color preservation than the control. When one of the four ingredients presented in Table 6 were not included, as seen in Comparative Compositions 1-4, the hair treatment composition did not provide significantly superior color preservation.

Example 4

The Exemplary Shampoo and Exemplary Composition B were applied to volunteers to assess the effect of such a combination on hair. Specifically, 21 volunteers had their hair highlighted by professional hair stylists. 14 volunteers had their hair shampooed with the Exemplary Shampoo, rinsed, and then conditioned with Exemplary Composition B. 7 of the volunteers had their hair shampooed with a commercial benchmark (Commercial Benchmark Shampoo 1), rinsed, and then conditioned with a commercial benchmark (Commercial Benchmark Conditioner 1).

Commercial Benchmark Shampoo 1 contains non-sulfate based anionic surfactants, decyl glucoside (alkyl polyglucosides), glycol distearate, alkoxylated fatty alcohol, ester, acrylates copolymer, plant extracts, plant oils, fragrance, chelants, preservatives, acids, and water. Commercial Benchmark Conditioner 1 contains cetearyl alcohol and cetyl alcohol (fatty alcohol), Behentrimonium Chloride and Cetrimonium Chloride (cationic surfactants), esters, amodomethicone (silicone), nonionic surfactants, plant extracts, plant oils, chelants, preservatives, fragrance, water.

The hair of the 21 volunteers was dried and then evaluated. It was determined that the volunteers that received the Exemplary Shampoo and Exemplary Composition B had notably improved hair characteristics, such as improved frizz control, better end seals, a silkier feel, and improved shine. These improved hair characteristics were obtained without weighing down the hair or interfering with the color highlighting of the hair.

Example 5

The Exemplary Shampoo and Exemplary Composition B were evaluated against commercial benchmarks. Four volunteers had half their head shampooed, rinsed, and conditioned with the Exemplary Shampoo and Exemplary Composition B and the other half with similar amounts of commercial benchmark products (Commercial Benchmark Shampoo 2 and Commercial Benchmark Conditioner 2).

Commercial Benchmark Shampoo 2 contains sodium laureth sulfate (anionic surfactant), cocamidopropyl betaine (amphoteric surfactant), glycol distearate (ester/opacifier), guar hydroxypropyltrimonium chloride (cationic polymer), salts, preservatives, colorants, pigments, glycerin, water.

Commercial Benchmark Conditioner 2 contains cetearyl alcohol (fatty alcohol), stearamidoethyl diethylamine behentrimonium chloride, cetrimonium chloride (cationic surfactants), amodimethicone (silicone)), preservatives, chelants, salt, acids, fragrance, colorants, water.

The hair of the volunteers was evaluated wet and after being dried. A table of the results for the evaluation of the volunteer's hair is provided in FIG. 1. Notably, the combination of the Example Shampoo and Example Composition B provided a silkier touch, improved suppleness, better sealed ends, and better shaping as compared to the combination of Commercial Benchmark Shampoo 2 and Commercial Benchmark Conditioner 2.

Example 6

The Exemplary Shampoo and Exemplary Composition B were evaluated against commercial benchmarks. Two volunteers had half their head shampooed, rinsed, and conditioned with the Exemplary Shampoo and Exemplary Composition B and the other half with similar amounts of commercial benchmark products (Commercial Benchmark Shampoo 3 and Commercial Benchmark Conditioner 3).

Commercial Benchmark Shampoo 3 contains Sodium Lauroyl Methyl Isethionate, Sodium Methyl Cocoyl Taurate (anionic surfactants), Cocamidopropyl Betaine (amphoteric surfactant), Glycol Distearate (ester/opacifier), esters, glycerides, polyquaternium, salts, preservatives, fragrance, chelants, water.

Commercial Benchmark Conditioner 3 contains cetearyl alcohol (fatty alcohol), behentrimonium chloride (cationis surfactant), guar hydroxypropyltrimonium chloride (cationic polymer), hydrolyzed protein, preservatives, salt, acids, fragrance, water.

The hair of the volunteer was evaluated wet and after being dried. The combination of the Example Shampoo and Example Composition B provided a silkier touch, better end seals, improved suppleness, and better shaping as compared to a combination of Commercial Benchmark Shampoo 3 and Commercial Benchmark Conditioner 3.

Example 7

The Exemplary Shampoo and Exemplary Composition B were evaluated against commercial benchmarks. Two volunteers had half their head shampooed, rinsed, and conditioned with the Exemplary Shampoo and Exemplary Composition B and the other half with similar amounts of commercial benchmark products (Commercial Benchmark Shampoo 4 and Commercial Benchmark Conditioner 4).

Commercial Benchmark Shampoo 4 contains non-sulfate based anionic surfactants, glycerin, cocamidopropyl betaine (amphoteric surfactant), glycol distearate, alkoxylated fatty alcohol, esters, acrylates/vinyl neodecanoate crosspolymer, quaternary compounds, neutralizing agents, plant extracts, plant oils, fragrance, chelants, preservatives, acids, and water.

Commercial Benchmark Conditioner 4 contains cetyl alcohol, stearyl alcohol (fatty alcohols), behentrimonium chloride, cetrimonium chloride, behentrimonium methosulfate (cationic surfactants), dimethicone, phenyl trimethicone, polysilicone-15 (silicones), guar hydroxypropyltrimonium chloride (cationic polymer), esters, hydrolyzed prototeins, plant extracts, plant oils, preservatives, fragrance, water.

The hair of the volunteer was evaluated wet and after being dried. The combination of Example Shampoo and Example Composition B provided a silkier touch, better end seals, improved suppleness, improved frizz control, and healthier feeling and looking hair compared to the combination of Commercial Benchmark Shampoo 4 and Commercial Benchmark Conditioner 4.

What is claimed is:

1. A hair treatment composition comprising:

(a) about 3 to about 6 wt. % of two or more cationic surfactants comprising:

(i) about 0.5 to 2.5 wt. % of dicetyldimonium chloride, and (ii) about 2.5 to about 4.8 wt. % of behentrimonium chloride;

(b) about 0.1 to about 2 wt. % of hydroxypropyl guar;

(c) about 10 wt. % to about 20 wt. % of one or more fatty alcohols;

(d) about 1 to about 4.5 wt. % of bis-cetearyl amodimethicone;

(e) about 50 to about 78 wt. % of water; and (f) about 1 wt. % to about 10 wt. % of one or more polyols;

wherein the hair treatment composition is an emulsion, the hair treatment composition is free from polymers formed from monomers of acrylic acid, its salts, or its esters, and all weight percentages are based on the total weight of the hair treatment composition.

2. A hair treatment composition comprising:

(a) about 3 to about 6 wt. % of two or more cationic surfactants comprising:

(i) about 0.5 to about 2.5 wt. % of a di-alkyl dimonium halide compound or salt thereof, and (ii) about 2.5 to about 4.8 wt. % of a mono-alkyl trimonium halide compound or salt thereof;

wherein (a)(i) and (a)(ii) are in a weight ratio of about 1:2 to about 1:6;

(b) about 0.1 to about 2 wt. % of hydroxypropyl guar;

(c) about 10 wt. % to about 20 wt. % of one or more of a fatty alcohols;

(d) about 1 to about 4.5 wt. % of bis-cetearyl amodimethicone;

(e) about 50 to about 78 wt. % of water; and (f) about 1 wt. % to about 10 wt. % of a polyol chosen from ethylene glycol, propylene glycol, butylene glycol, hexylene glycol, pentylene glycol, diethylene glycol, dipropylene glycol, caprylyl glycol, 1,3 propanediol, glycerin, diglycerin, polyethylene glycols, and a mixture thereof;

wherein the hair treatment composition is an emulsion, the hair treatment composition is free from polymers formed from monomers of acrylic acid, its salts, or its esters, and all weight percentages are based on the total weight of the hair treatment composition.

3. The hair treatment composition of claim 1, wherein (a)(i) and (a)(ii) are in a weight ratio of about 1:2 to about 1:5.

4. The hair treatment composition of claim 3, wherein the two or more cationic surfactants further comprise cetrimonium chloride.

5. The hair treatment composition of claim 3, wherein the one or more polyols are selected from ethylene glycol, propylene glycol, butylene glycol, hexylene glycol, pentylene glycol, diethylene glycol, dipropylene glycol, caprylyl glycol, 1,3 propanediol, glycerin, and diglycerin.

6. The hair treatment composition of claim 5, wherein the one or more polyols are in an amount of about 3 to about 8 wt. %.

7. The hair treatment composition of claim 6, wherein the one or more polyols is glycerin.

8. The hair treatment composition of claim 7, further comprising one or more fatty compounds selected from fatty esters and waxes.

9. The hair treatment composition of claim 2, wherein the two or more cationic surfactants further comprise cetrimonium chloride.

10. The hair treatment composition of claim 2, wherein the one or more polyols are in an amount of about 3 to about 8 wt. %.

11. The hair treatment composition of claim 10, wherein the one or more polyols is glycerin.

12. The hair treatment composition of claim 11, further comprising one or more fatty compounds selected from fatty esters and waxes.

13. A hair treatment composition comprising:

(a) about 2 to about 6 wt. % of two or more cationic surfactants comprising:

(i) about 1 to about 2 wt. % of dicetyldimonium chloride, and (ii) behentrimonium chloride, wherein (a)(i) and (a)(ii) are in a weight ratio of about 1:2 to about 1:5;

(b) about 0.1 to about 4 wt. % of hydroxypropyl guar;

(c) about 10 wt. % to about 20 wt. % of one or more fatty alcohols;

(d) about 3 to about 7 wt. % of a mixture of silicones, the mixture of silicones consisting of bis-cetearyl amodimethicone, dimethicone, and amodimethicone, wherein the bis-cetearyl amodimethicone is in an amount of about 1 to about 4.5 wt. %;

(e) about 50 to about 78 wt. % of water; and (f) about 1 wt. % to about 10 wt. % of one or more polyols;

wherein the hair treatment composition is an emulsion, the hair treatment composition is free from polymers formed from monomers of acrylic acid, its salts, or its esters, its salts, or its esters, the only silicones in the hair treatment composition is the mixture of silicones consisting of the bis-cetearyl amodimethicone, the dimethicone, and the amodimethicone, and all weight percentages are based on the total weight of the hair treatment composition.

14. The hair treatment composition of claim 13, wherein the one or more polyols are selected from ethylene glycol, propylene glycol, butylene glycol, hexylene glycol, pentylene glycol, diethylene glycol, dipropylene glycol, caprylyl glycol, 1,3 propanediol, glycerin, and diglycerin.

15. The hair treatment composition of claim 14, wherein the one or more polyols are in an amount of about 3 to about 8 wt. %.

16. The hair treatment composition of claim 15, wherein the one or more polyols is glycerin.

17. The hair treatment composition of claim 13, wherein the composition is free from polyquaternium compounds.

* * * * *